United States Patent [19]
Li et al.

[11] Patent Number: 6,083,925
[45] Date of Patent: Jul. 4, 2000

[54] NUCLEIC ACID RESPIRATORY SYNCYTIAL VIRUS VACCINES

[75] Inventors: Xiaomao Li, Toronto; Mary E. Ewasyshyn, Thornhill; Suryaprakash Sambhara, Markham; Michel H. Klein, Willowdale, all of Canada

[73] Assignee: Connaught Laboratories Limited, North York, Canada

[21] Appl. No.: 09/262,927

[22] Filed: Mar. 5, 1999

Related U.S. Application Data

[63] Continuation-in-part of application No. 08/896,500, Jul. 18, 1997, Pat. No. 6,017,897, which is a continuation-in-part of application No. 08/659,939, Jun. 7, 1996, Pat. No. 5,843,913, which is a continuation-in-part of application No. 08/476,397, Jun. 7, 1995, Pat. No. 6,019,980.

[51] Int. Cl.[7] .......................... C12N 15/64; A61K 31/70
[52] U.S. Cl. ........................................... 514/44; 435/91.4
[58] Field of Search ...................... 424/211.1; 435/69.1, 435/69.3, 91.4; 514/44

[56] References Cited

U.S. PATENT DOCUMENTS

| | | | |
|---|---|---|---|
| 5,149,650 | 9/1992 | Wertz et al. | 435/243 |
| 5,589,466 | 12/1996 | Felgner et al. | 514/44 |

FOREIGN PATENT DOCUMENTS

| | | |
|---|---|---|
| WO 90/11092 | 10/1990 | WIPO . |
| WO 92/07940 | 5/1992 | WIPO . |
| WO 93/21310 | 10/1993 | WIPO . |
| WO 94/21797 | 9/1994 | WIPO . |

OTHER PUBLICATIONS

Katz, S.L.New Vaccine Development establishing priorities. vol. 1. Washington: National Academic Press: 1985 397–409.
Pemberton et al., J. Gen. Virol. 1987, 68:2177–2182.
Pizzorno et al., J. Virol. Acids Res. 1988, G2:1167–1179.
Green, S. et al., Nucl. Acids Res. 1988, 16:369.
Breathnack, R. et al., Nucl. Acids Res. 1983, 11:7119–7136.
Karasuyama & Melchers, Eur. J. Immunol. 18, 97–104, 1988.
Wilde, David B. et al., 1983, J. Immunol. 131:2178–2183.
Ledbetter, J.A. et al 1980, J. Exp. Med. 152:280–295.
Ozato Keiko et al, 1982, Transplantation 34:113–118.
Prince et al, J. Virol., 61:1851–1854. (1987).
Hemming et al, J. Infect. Dis., 152:1083–1087 (1985).
McIntosh, K. Et al In: Fields BN, Knipe, DM, editors. Virology, New York: Raven Press 1990:1045–1072.
Wertz, G.W. et al, Biotechnology 1992, 20:151–176.
Johnson et al., J. Virol. 1987, 61: 3163–3165.
Crowe, J.E., Vaccine 1995, 13:415–421.
Ulmer, Current Opinion, Invest Drugs, 1993, 2:983–989.
Tang et al., Nature 1992, 356: 152–154.
Furth et al. Analytical Biochemistry, 1992, 205: 365–368.
Chapman, B.S. et al, Nucl. Acids Res. 1991, 19: 3979–3986.
Graham, B.S. et al., J. Mod. Virol. 1988 26: 153–162.
Nabel, G.J. et al Proc. Natl. Acad. Sci. USA 90:11307–11311 (1993).
Du, R.P. et al 1994, Biotechnology 12: 813–818.
Prince, G.A. et al, 1978. Ame J. Pathol. 93: 771–790.
Davis et al, Vaccine 1994, 12: 1503–1509.
Chanock, Robert M. et al, Pediatrics vol. 90 No. 1, July 1992, pp 137–142.
Prince et al, J. Virol. 55:517;1985 Virus Res. 3; 193–206.
Groothuis et al, N. Engl. J. Med. 329:1524–1530, (1993).
Walsh et al, J. Infec. Dis., 155: 1198–1204, (1987)
Paradiso et al, Pediatr. Infect. Dis. J. 13:792–798, (1994).
Lounsbach et al, Journal of General Virology 74, 2559–2565 (1993).
Wathen et al, J. Infect. Dis. 159: 255–264 (1989).
Wertz et al, J. Virol 61: 293–301 (1987).
Tang et al (1993) J. Biol. Chem. 268:9522–9525.
Collis et al (1990) Embo J. 9:233–240.

*Primary Examiner*—Robert A. Schwartzman
*Attorney, Agent, or Firm*—Sim & McBurney

[57] ABSTRACT

Non-replicating vectors containing a nucleotide sequence coding for an F protein of respiratory syncytial virus (RSV) and a promoter for such sequence, preferably a cytomegalovirus promoter, are described for in vivo immunization. The nucleotide sequence enclboding the RSV F protein may lack a sequence encoding the homologous signal peptide but possessing a heterologous signal peptide enhancing RSV F protein expression. Such non-replicating vectors, including plasmids, also may contain a further nucleotide sequence located adjacent to the RSV F protein encoding sequence to enhance the immunoprotective ability of the RSV F protein when expressed in vivo. Such non-replicating vectors may be used to immunize a host against disease caused by infection with RSV, including a human host, by administration thereto, and may be formulated as immunogenic compositions with pharmaceutically-acceptable carriers for such purpose. Such vectors also may be used to produce antibodies for detection of RSV infection in a sample.

25 Claims, 39 Drawing Sheets

FIG. 2A.

NUCLEOTIDE SEQUENCE OF THE RSV F GENE.

←——— SP ———→

5'
MET GLU LEU PRO ILE LEU LYS ALA ASN ALA ILE THR THR ILE LEU ALA ALA VAL THR PHE
ATGGAGTTGCCAATCCTCAAAGCAAATGCAATTACCACAATCCTCGCTGCAGTCACATTT
TACCTCAACGGTTAGGAGTTTCGTTTACGTTAATGGTGTTAGGAGCGACGTCAGTGTAAA
         10        20        30        40        50        60

CYS PHE ALA SER SER GLN ASN ILE THR GLU GLU PHE TYR GLN SER THR CYS SER ALA VAL
TGCTTTGCTTCTAGTCAAAACATCACTGAAGAATTTTATCAATCAACATGCAGTGCAGTT
ACGAAACGAAGATCAGTTTTGTAGTGACTTCTTAAAATAGTTAGTTGTACGTCACGTCAA
         70        80        90       100       110       120

SER LYS GLY TYR LEU SER ALA LEU ARG THR GLY TRP TYR THR SER VAL ILE THR ILE GLU
AGCAAAGGCTATCTTAGTGCTCTAAGAACTGGTTGGTATACTAGTGTTATAACTATAGAA
TCGTTTCCGATAGAATCACGAGATTCTTGACCAACCATATGATCACAATATTGATATCTT
        130       140       150       160       170       180

LEU SER ASN ILE LYS GLU ASN LYS CYS ASN GLY THR ASP ALA LYS VAL LYS LEU MET LYS
TTAAGTAATATCAAGGAAAATAAGTGTAATGGAACAGATGCTAAGGTAAAATTGATGAAA
AATTCATTATAGTTCCTTTATTCACATTACCTTGTCTACGATTCCATTTTAACTACTTT
        190       200       210       220       230       240

GLN GLU LEU ASP LYS TYR LYS ASN ALA VAL THR GLU LEU GLN LEU MET GLN SER THR
CAAGAATTAGATAAATATAAAAATGCTGTAACAGAACTGCAGTTGCTCATGCAAAGCACA
GTTCTTAATCTATTTATATTTTACGACATTGTCTTGACGTCAACGAGTACGTTTCGTGT
        250       260       270       280       290       300

PRO ALA ALA ASN ASN ARG ALA ARG ARG GLU LEU PRO ARG PHE MET ASN TYR THR LEU ASN
CCAGCAGCAAACAATCGAGCCAGAAGAGAACTACCAAGGTTTATGAATTATACACTCAAC
GGTCGTCGTTTGTTAGCTCGGTCTTCTCTTGATGGTTCCAAATACTTAATATGTGAGTTG
        310       320       330       340       350       360

FIG.2B.

```
                                                                                   F2-F1CLEAVAGE SITE
ASN THR LYS LYS THR ASN VAL THR LEU SER LYS LYS ARG LYS ARG↓PHE LEU GLY PHE
AATACCAAAAAAACCAATGTAACATTAAGCAAGAAAAGAAAA&AAGATTTCTTGGTTTT
TTATGGTTTTTGGTTACATTGTAATCGTTCTTTCCTTTCTTCTTTCTAAAGAACCAAAA
          370       380       390       400       410       420

LEU LEU GLY VAL GLY SER ALA ILE ALA SER GLY ILE ALA VAL SER LYS VAL LEU HIS LEU
TTGTTAGGTGTTGGATCTGCAATCGCCAGTGGCATTGCTGTGTATCTAAGGTCCTGCACTTA
AACAATCCACACCTAGACGTTAGCGGTCACCGTAACGACATAGATTCCAGGACGTGAAT
          430       440       450       460       470       480

GLU GLY VAL ASN LYS ILE LYS SER ALA LEU LEU SER THR ASN LYS ALA VAL VAL SER
GAAGGAGAAGTGAACAAGATCAAAAGTGCTCTACTATCCACAAACAAGGCCGTAGTCAGC
CTTCCTCTTCACTTGTTCTAGTTTTCACGAGATAGGTGTTTGTTCCGGCATCAGTCG
          490       500       510       520       530       540

LEU SER ASN GLY VAL SER VAL LEU THR SER LYS VAL LEU ASP LEU LYS ASN TYR ILE ASP
TTATCAAATGGAGTTAGTGTCTTAACCAGCAAAGTGTTAGACCTCAAAAACTATATAGAT
AATAGTTTACCTCAATCACAGAATTGGTCGTTTCACAATCTGGAGTTTTGATATATCTA
          550       560       570       580       590       600

LYS GLN LEU LEU PRO ILE VAL ASN LYS GLN SER CYS ARG ILE SER ASN ILE GLU THR VAL
AAACAATTGTTACCTATTGTGAATAAGCAAAGCTGCAGAATATCAAATATAGAAACTGTG
TTTGTTAACAATGGATAACACTTATTCGTTTCGACGTCTTATAGTTTATATCTTTGACAC
          610       620       630       640       650       660

ILE GLU PHE GLN HIS LYS ASN ASN ARG LEU LEU GLU ILE THR ARG GLU PHE SER VAL ASN
ATAGAGTTCCAACAACACCTGTAAGCACTTACATGTTAACTAATAATAGTGAATTTAGTGTTAAT
TATCTCAAGGTTGTTGTTTCTTGTGGATCTCTAATGGTCCCTTAAATCACAATTA
          670       680       690       700       710       720

ALA GLY VAL THR THR PRO VAL SER THR TYR MET LEU THR ASN SER GLU LEU LEU SER LEU
GCAGGTGTAACTACACCTGTAAGCACTTACATGTTAACTAATAGTGAATTATTGTCATTA
CGTCCACATTGATGTGGACATTCGTGAATGTACAATTGATTATCACTTAATAACAGTAAT
          730       740       750       760       770       780
```

FIG.2C.

```
ILE ASN ASP MET PRO ILE THR ASN ASP GLN LYS LYS LEU MET SER ASN ASN VAL GLN ILE
ATCAATGATATGCCTATAACAAATGATCAGAAAAAGTTAATGTCCAACAATGTTCAAATA
           790            800            810            820            830            840

VAL ARG GLN GLN SER TYR SER ILE MET SER ILE ILE LYS GLU VAL LEU ALA TYR VAL
GTTAGACAGCAAAGTTACTCTATCATGTCCATAATAAAAGAGGAAGTCTTAGCATATGTA
           850            860            870            880            890            900

VAL GLN LEU PRO LEU TYR GLY VAL ILE ASP THR PRO CYS TRP LYS LEU HIS THR SER PRO
GTACAATTACCACTATATGGTGTGATAGATACACCTTGTTGGAAATTACACACATCCCCT
           910            920            930            940            950            960

LEU CYS THR THR ASN THR LYS GLU GLY SER ASN ILE CYS LEU THR ARG THR ASP ARG GLY
CTATGTACAACCACAACAAAAGAAGGTCAAACATCTGTTAACAAGAACTGACAGAGGA
           970            980            990           1000           1010           1020

TRP TYR CYS ASP ASN ALA GLY SER VAL SER PHE PHE PRO GLN ALA GLU THR CYS LYS VAL
TGGTACTGTGACAATGCAGGATCAGTATCTTCTTCCCACAAGCTGAAACATGTAAAGTT
          1030           1040           1050           1060           1070           1080

GLN SER ASN ARG VAL PHE CYS ASP THR MET ASN SER LEU THR LEU PRO SER GLU VAL ASN
CAATCGAATCGAGTATTTGTGACACAATGAACAGTTAACATTACCAAGTGAAGTAAAT
          1090           1100           1110           1120           1130           1140

LEU CYS ASN VAL ASP ILE PHE ASN PRO LYS TYR ASP CYS LYS ILE MET THR SER LYS THR
CTCTGCAATGTTGACATATTCAATCCCAAATATGATTGTAAAATTATGACTTCAAAACA
          1150           1160           1170           1180           1190           1200
```

```
     LEU ILE ALA VAL GLY LEU LEU LEU TYR CYS LYS ALA ARG SER THR LYS ALA ARG SER THR LEU SER
                                              ↑
TTAATTGCTGTTGGACTGCTCCTATACTGTAAGGCCAGAAGCACCAGTCACACTAAGC
AATTAACGACAACCTGACGAGGATATGACATTCCGGTCTTCGTGGTCAGTGTGATTCG
     1630              1640              1650              1660              1670              1680

LYS, ASP GLN LEU SER GLY ILE ASN ASN ILE ALA PHE SER ASN
AAGGATCAACTGAGTGGTATAAATAATATTGCATTTAGTAACTGAATAAAAATAGCACCT
TTCCTAGTTGACTCACCATATTTATTATAACGTAAATCATTGACTTATTTTATCGTGGA
     1690              1700              1710              1720              1730              1740

AATCATGTTCTTACAATGGTTTACTATCTGCTCATAGACAACCCATCTATCATTGGATTT
TTAGTACAAGAATGTTACCAAATGATAGACGAGTATCTGTTGGGTAGATAGTAACCTAAA
     1750              1760              1770              1780              1790              1800

TCTTAAAATCTGAACTTCATCGAAACTCTTATCTATAAACCATCTCACTTACACTATTTA
AGAATTTTAGACTTGAAGTAGCTTTGAGAATAGATATTTGGTAGAGTGAATGTGATAAAT
     1810              1820              1830              1840              1850              1860

3'
AGTAGATTCCTAGTTTATAGTTATAT
TCATCTAAGGATCAAATATCAATATA
     1870              1880
```

NUCLEOTIDE SEQUENCE OF THE RSV F GENE. THE cDNA SEQUENCE IS SHOWN IN THE PLUS (mRNA) STRAND SENSE IN THE 5' TO 3' DIRECTION. THE SIGNAL PEPTIDE (SP) AND THE TRANSMEMBRANE (TM) ANCHOR DOMAIN ARE UNDERLINED. THE PREDICTED F2-F1 CLEAVAGE SITE IS INDICATED BY THE ARROW (↓).

FIG. 3A.

NUCLEOTIDE SEQUENCE OF THE RSV F GENE.

```
         ←——————————————— SP ———————————————
5'  MET GLU LEU PRO ILE LEU LYS ALA ASN ALA ILE THR THR ILE LEU ALA ALA VAL THR PHE
    ATG GAG TTG CCA ATC CTC AAA GCA AAT GCA ATT ACC ACA TCC TCG CTG CAG TCA CAT TT
    TAC CTC AAC GGT TAG GAG TTT CGT TTA CGT TAA TGG TGT AGG AGC GAC GTC AGT GTA AAA
          10              20              30              40              50              60

CYS PHE ALA SER SER GLN ASN ILE THR GLU GLU PHE TYR GLN SER THR CYS SER ALA VAL
    TGC TTT GCT TCT AGT GCT CTA GTC AAA ACA TCA CTG AAG AAT TTT ATC AAT CAA CAT GCA GTT
    ACG AAA CGA AGA TCA CGA GAT CAG TTT TGT AGT GAC TTC TTA AAG ATC AGT TAG TTG TAC GTC AA
          70              80              90             100             110             120

SER LYS GLY TYR LEU SER ALA LEU ARG THR GLY TRP TYR THR SER VAL ILE THR ILE GLU
    AGC AAA GGC TAT CTT AGT GCT CTA AGA ACT GGT TGG TAT ACT AGT GTT ATA ACT ATA GAA
    TCG TTT CCG ATA GAA TCA CGA GAT TCT TGA CCA ACC ATA TGA TCA CAA TAT TGA TAT CTT
          130             140             150             160             170             180

LEU SER ASN ILE LYS GLU ASN LYS CYS ASN GLY THR ASP ALA LYS VAL LYS LEU MET LYS
    TTA AGT AAT ATC AAG GAA AAT AAG TGT AAT GGA ACA GAT GCT AAG GTA AAA TTG ATG AAA
    AAT TCA TTA TAG TTC CTT TTA TTC ACA TTA CCT TGT CTA CGA TTC CAT TTT AAC TAC TTT
          190             200             210             220             230             240

GLN GLU LEU ASP LYS TYR LYS ASN ALA VAL THR GLU LEU GLN LEU LEU MET GLN SER THR
    CAA GAA TTA GAT AAA TAT AAA AAT GCT GTA ACA GAA TTG CAG TTG CTC ATG CAA AGC ACA
    GTT CTT AAT CTA TTT ATA TTT TTA CGA CAT TGT CTT AAC GTC AAC GAG TAC GTT CGT GT
          250             260             270             280             290             300

PRO ALA ALA ASN ASN ARG ALA ARG ARG GLU LEU PRO ARG PHE MET ASN TYR THR LEU ASN
    CCA GCA GCA AAC AAT CGA GCC AGA AGA GAA CTA CCA AGG TTT ATG AAT TAT ACA CTC AAC
    GGT CGT CGT TTG TTA GCT CGG TCT TCT CTT GAT GGT TCC AAA TAC TTA ATA TGT GAG TTG
          310             320             330             340             350             360
```

FIG. 3B.

```
                                                                   F2-F1CLEAVAGE SITE
ASN THR LYS LYS THR ASN VAL THR LEU SER LYS LYS ARG LYS ARG ARG↓PHE LEU GLY PHE
AATACCAAAAAAACCAATGTAACATTAAGCAAGAAAAAGGAAAAAGAAAA8AAGATTTCTTGGTTTT
         370           380           390           400           410           420

LEU LEU GLY VAL GLY SER ALA ILE ALA SER GLY ILE ALA VAL SER LYS VAL LEU HIS LEU
TTGTTAGGTGTTGGATCTGCAATCGCCAGTGGCATTGCTGTATCTAAGGTCCTGCACTTA
AACAATCCACACCTAGACGTTAGCGGTCACCGTAACGACATAGATTCCAGGACGTGAAT
         430           440           450           460           470           480

GLU GLY GLU VAL ASN LYS ILE LYS SER ALA LEU LEU SER THR ASN LYS ALA VAL VAL SER
GAAGGAGAAGTGAACAAGATCAAAAGTGCTCTACTATCCACAAACAAGGCCGTAGTCAGC
CTTCCTCTTCACTTGTTCTAGTTTTCACGAGATGATAGGTGTTGTTCCGGCATCAGTCG
         490           500           510           520           530           540

LEU SER ASN GLY VAL SER VAL LEU THR SER LYS VAL LEU ASP LEU LYS ASN TYR ILE ASP
TTATCAAATGGAGTTAGTGTCTTAACCAGCAAAGTGTTAGACCTCAAAAACTATATAGAT
AATAGTTTACCTCAATCACAGAATTGGTCGTTTCACAATCTGGAGTTTTGATATATCTA
         550           560           570           580           590           600

LYS GLN LEU LEU PRO ILE VAL ASN LYS GLN SER CYS ARG ILE SER ASN ILE GLU THR VAL
AAACAATTGTTACCTATTGTGAATAAGCAAAGCTGCAGAATATCAAATATAGAAACTGTG
TTTGTTAACAATGGATAACACTTATTCGTTTCGACGTCTTATAGTTTATATCTTTGACAC
         610           620           630           640           650           660

ILE GLU PHE GLN HIS LYS ASN ASN ARG LEU LEU GLU ILE THR ARG GLU PHE SER VAL ASN
ATAGAGTTCCAACAAAAGAACAACAGACTAGAGATTACCAGGGAATTAGTGTTAAT
TATCTCAAGGTTGTTTTCTTGTTGTCTGATGATCTCTAATGGTCCCTTAAATCACAATTA
         670           680           690           700           710           720

ALA GLY VAL THR THR PRO VAL SER THR TYR MET LEU THR ASN SER GLU LEU LEU SER LEU
GCAGGTGTAACTACACCTGTAAGCACTTACATGTTAACTAATAGTGAATTATTGTCATTA
CGTCCACATTGATGTGGACATTCGTGAATGTACAATTGATTATCACTTAATAACAGTAAT
         730           740           750           760           770           780
```

FIG.3C.

```
ILE ASN ASP MET PRO ILE THR ASN ASP GLN LYS LYS LEU MET SER ASN ASN VAL GLN ILE
ATCAATGATATGCCTATAACAAATGATCAGAAAAAGTTAATGTCCAACAATGTTCAAATA
         790                800                810                820                830                840

VAL ARG GLN SER TYR SER ILE MET SER ILE ILE LYS GLU GLU VAL LEU ALA TYR VAL
GTTAGACAGAGCAAAGTTACTCTATCATGTCCATAATAAAGAGGAAGTCTTAGCATATGTA
         850                860                870                880                890                900

VAL GLN LEU PRO LEU TYR GLY VAL ILE ASP THR PRO CYS TRP LYS LEU HIS THR SER PRO
GTACAATTACCACTATATGGTGTGATAGATACACCTTGTTGGAAATTACACACATCCCT
         910                920                930                940                950                960

LEU CYS THR THR ASN THR LYS GLU GLY SER ASN ILE CYS LEU THR ARG THR ASP ARG GLY
CTATGTACAACCAACACAAAGAAGGGTCAAACATCTGTTTAACAAGAACTGACAGAGGA
         970                980                990                1000               1010               1020

TRP TYR CYS ASP ASN ALA GLY SER VAL SER PHE PHE PRO GLN ALA GLU THR CYS LYS VAL
TGGTACTGTGACAATGCAGGATCAGTATCTTTCTTCCCACAAGCTGAAACATGTAAAGTT
         1030               1040               1050               1060               1070               1080

GLN SER ASN ARG VAL PHE CYS ASP THR MET ASN SER LEU THR LEU PRO SER GLU VAL ASN
CAATCGAATCGAGTATTTGTGACACAATGAACAGTTTAACATTACCAAGTGAAGTAAAT
         1090               1100               1110               1120               1130               1140

LEU CYS ASN VAL ASP ILE PHE ASN PRO LYS TYR ASP CYS LYS ILE MET THR SER LYS THR
CTCTGCAATGTTGACATATTCAATCCAAATATGATTGTAAAATTATGACTTCAAAAACA
         1150               1160               1170               1180               1190               1200
```

FIG.3D.

```
ASP VAL SER SER VAL ILE THR SER LEU GLY ALA ILE VAL SER CYS TYR GLY LYS THR
GATGTAAGCAGCTCCGTTATCACATCTCTAGGAGCCATTGTGTCATGCTATGGCAAAACT
CTACATTCGTCGAGGCAATAGTGTAGAGATCCTCGGTAACACAGTACGATACCGTTTGA
       1210         1220         1230         1240         1250         1260

LYS CYS THR ALA SER ASN LYS ASN ARG GLY ILE ILE LYS THR PHE SER ASN GLY CYS ASP
AAATGTACAGCATCCAATAAAAATCGTGGAATCATAAAGACATTTCTAACGGGTGTGAT
TTTACATGTCGTAGGTTATTTTTAGCACCTTAGTATTTCTGTAAAGATTGCCCACACTA
       1270         1280         1290         1300         1310         1320

TYR VAL SER ASN LYS GLY VAL ASP THR VAL SER VAL GLY ASN THR LEU TYR TYR VAL ASN
TATGTATCAAATAAAGGGGTGGACACTGTGTCTGTAGGTAACACATTATATTATGTAAAT
ATACATAGTTTATTTCCCACCTGTGACACAGATCCATTGTAATATAATACATTTA
       1330         1340         1350         1360         1370         1380

LYS GLN GLU GLY LYS SER LEU TYR VAL LYS GLY GLU PRO ILE ILE ASN PHE TYR ASP PRO
AAGCAAGAAGGCAAAAGTCTCTATGTAAAAGGTGAACCAATAAJAAATTTCTATGACCCA
TTCGTTCTTCCGTTTTCAGAGATACATTTCCACTTGGTTATTATTTAAAGATACTGGGT
       1390         1400         1410         1420         1430         1440

LEU VAL PHE PRO SER ASP ALA SER ILE SER GLN VAL ASN GLU LYS ILE ASN
TTAGTATTCCCTCTGATGCATCAATATCTCAAGTCAATGAGAAGATTAAC
AATCATAAGGGAGACTACTTAAACTACGTAGTTATAGAGTTCAGTTACTCTTCTAATTG
       1450         1460         1470         1480         1490         1500

GLN SER LEU ALA PHE ILE LEU ARG LYS SER ASP GLU LEU LEU HIS ASN VAL ASN ALA GLY LYS
CAGAGTTTAGCATTTATTCGTAAATCCGATGAATTATTACATAATGTAAATGCTGGTAAA
GTCTCAAATCGTAAATAAAGCATTTAGGCTACTTAATAATGTATTACACATTTACGACCATTT
       1510         1520         1530         1540         1550         1560

SER THR THR ASN ILE MET Thr Stop Stop Stop Bam HI
TCAACCACAAATATCATGACTTGATAATGAGGATCC
AGTTGGTGTTTATAGTACTGAACTATTACTCCTAGG
       1570
```

FIG.8

```
401  TTGGGGACCC  TTGATTGTTC  TTTCTTTTTC  GCTATTGTAA  AATTCATGTT
451  ATATGGAGGG  GGCAAAGTTT  TCAGGGTGTT  GTTAGAATG   GGAAGATGTC
501  CCTTGTATCA  CCATGGACCC  TCATGATAAT  TTTGTTTCTT  TCACTTTCTA
551  CTCTGTGTAC  AACCATTGTC  TCCTCTTATT  TTCTTTTCAT  TTTCTGTAAC
601  TTTTTCGTTA  AACTTTAGCT  TGCATTTGTA  ACGAATTTTT  AAATTCACTT
651  TTGTTTATTT  GTCAGATTGT  AAGTACTTTC  TCTAATCACT  TTTTTTTCAA
701  GGCAATCAGG  GTATATTATA  TTGTACTTCA  GCACAGTTTT  AGAGAACAAT
751  TGTTATAATT  AAATGATAAG  GTAGAATATT  TCTGCATATA  AATTCTGGCT
801  GGCGTGGAAA  TATTCTTATT  GGTAGAAACA  ACTACATCCT  GGTCATCATC
851  CTGCCTTCT   CTTTATGGTT  ACAATGATAT  ACACTGTTTG  AGATGAGGAT
901  AAAATACTCT  GAGTCCAAAC  CGGGCCCCTC  TGCTAACCAT  GTTCATGCCT
951  TCTTCTTTTT  CCTACAG
```

GTGAGT

FIG. 11A

Nucleotide Sequence of plasmid VR1012

```
         10         20         30         40         50         60         70
TCGCGCGTTT CGGTGATGAC GGTGAAAACC TCTGACACAT GCAGCTCCCG GAGACGGTCA CAGCTTGTCT 80         90        100        110        120        130        140
GTAAGCGGAT GCCGGGAGCA GACAAGCCCG TCAGGGCGCG TCAGCGGGTG TTGGCGGGTG TCGGGGCTGG 150        160        170        180        190        200        210
CTTAACTATG CGGCATCAGA GCAGATTGTA CTGAGAGTGC ACCATATGCG GTGTGAAATA CCGCACAGAT 220        230        240        250        260        270        280
GCGTAAGGAG AAAATACCGC ATCAGATTGG CTATTGGCCA TTGCATACGT TGTATCCATA TCATAATATG 290        300        310        320        330        340        350
TACATTTATA TTGGCTCATG TCCAACATTA CCGCCATGTT GACATTGATT ATTGACTAGT TATTAATAGT 360        370        380        390        400        410        420
AATCAATTAC GGGGTCATTA GTTCATAGCC CATATATGGA GTTCCGCGTT ACATAACTTA CGGTAAATGG 430        440        450        460        470        480        490
CCCGCCTGGC TGACCGCCCA ACGACCCCCG CCCATTGACG TCAATAATGA CGTATGTTCC CATAGTAAG
```

FIG.11B

```
       500        510        520        530        540        550        560
CCAATAGGA  CTTTCCATTG  AGTTCAATGG  GTGGAGTATT  TACGGTAAAC  TGCCCACTTG  GCAGTACATC 570        580        590        600        610        620        630
AAGTGTATCA  TATGCCAAGT  AGCCCCCCTA  TTGAGTCAA   TGACGGTAAA  TGCCCGCCT   GGCATTATGC 640        650        660        670        680        690        700
CCAGTACATG  ACCTTATGGG  ACTTTCCTAC  TTGGCAGTAC  ATCTAGTAT   TAGTCATGGC  TATTACCATG 710        720        730        740        750        760        770
GTGATGCGGT  TTTGGCAGTA  CATCAATGGG  CGTGGATAGC  GGTTTGACTC  ACGGGGATTT  CCAAGTCTCC 780        790        800        810        820        830        840
ACCCCATTGA  CGTCAATGGG  AGTTTGTTTT  GGCACCAAAA  TCAACGGGAC  TTTCCAAAAT  GTGTAACAA 850        860        870        880        890        900        910
CTCCGCCCA   TTGACGCAAA  TGGGCGGTAG  GCGTGTACGG  TGGGAGGTCT  ATATAAGCAG  AGCTGTTTA 920        930        940        950        960        970        980
GGAACGGTC   AGATCGCCTG  GAGACGCCAT  CCACGCTGTT  TTGACCTCCA  TAGAAGACAC  CGGGACCGAT 990       1000       1010       1020       1030       1040       1050
CCAGCCTCCG  CGGCCGGGAA  CGGTGCATTG  GAACGCGGAT  TCCCCGTGCC  AAGAGTGACG  TAAGTACCGC
```

FIG.11C

```
      1060       1070       1080       1090       1100       1110       1120
CTATAGACTC TATAGGCACA CCCCTTTGC TCTTTATGCAT GCTATACTGT TTTTGGCCTTG GGGCCTATAC 1130       1140       1150       1160       1170       1180       1190
ACCCCCGCTT CCCTTATGCTA TAGGTGATGG TATAGCTTAG CCTATAGGTG TGGGTTATTG ACCATTATTG 1200       1210       1220       1230       1240       1250       1260
ACCACTCCCC TATTGTGTGAC GATACTTTCC ATTACTAATC CATAAACATGG CTCTTTTGCCA CAACTATCTC 1270       1280       1290       1300       1310       1320       1330
TATTGGCTAT ATGCCAATAC TCTGTCCTTC AGAGACTGAC ACGGACTCTG TATTTTTACA GGATGGGGTC 1340       1350       1360       1370       1380       1390       1400
CCATTATTA TTTACAAATT CACATATACA ACAAGCGCGT CCCCGTGCC CGCAGTTTTT ATTAAACATA 1410       1420       1430       1440       1450       1460       1470
GGGTGGGATC TCCAGGGGAA TCTCGGTAC GTGTTCCGA CATGGGCTCT TCTCGGTAG CGGGGAGCT 1480       1490       1500       1510       1520       1530       1540
TCCACATCCG AGCCCTCCC CCATGCCTCC AGGGCTCAT GGTCGCTGG CAGCTCCTTG CTCCTAACAG 1550       1560       1570       1580       1590       1600       1610
TGGAGCCAG ACTTAGGCAC AGCACAATGC CCACCACCAC CAGTGTGCCG CACAAGCCG TGGGGTAGG
```

FIG.11D

```
      1620       1630       1640       1650       1660       1670       1680
GTATGTGTCT GAAAATGAGC GTGGAGATTG GGCTCGCACG GCTTGAGCAG ATGGAAGACT TAAGGCAGCG 1690       1700       1710       1720       1730       1740       1750
GCAGAGAAG ATGCAGGCAG CTGAGTTGT CTGATTCTGT GTATTCTGAT AAGAGTCAGA GGTAACTCCC GTTGGGGTGC 1760       1770       1780       1790       1800       1810       1820
TGTTAACGT GCAGGGCAGT GTAGTCTGAG CAGTACTCGT TGCTGCCGG CCGGCCACCA GACATAATAG 1830       1840       1850       1860       1870       1880       1890
CTGACAGACT AACAGACTGT TCCTTTCCAT GGGTCTTTTC TGCAGTCACC GTCGTCGACA CGTGTGATCA 1900       1910       1920       1930       1940       1950       1960
GATATCGCGG CCCCTCTAGA GGATCCAGAT CTGCTGTGCC TTCTAGTTGC CAGCCATCTG 1970       1980       1990       2000       2010       2020       2030
TTGTTTGCCC CTCCCCCGTG CCTTCCCTTGA CCCTGGAAGG TGCCACTCCC ACTGTCCTTT CCTAATAAAA 2040       2050       2060       2070       2080       2090       2100
TGAGGAAATT GCATGCATT GTCTGAGTAG GTGTCATTCT ATTCTGGGGG GTGGGGGTGG GCAGACAGC 2110       2120       2130       2140       2150       2160       2170
AAGGGGAGG ATTGGAAGA CAATAGCAGG CATGCTGGGG ATGCGGTGG GCTCTATGGT ACCCAGTGC
```

FIG. 11E

```
     2180       2190       2200       2210       2220       2230       2240
TGAAGAATTG ACCCGGTTCC TCCTGGGCCA GAAAGAAGCA GGCACATCCC CTTCTCTGTG ACACACCTTG 2250       2260       2270       2280       2290       2300       2310
TCCAGCCCCC TGTTTCTTAG TTCCAGCCCC ACTCATAGGA CACTCATAGC TCAGGAGGC TCCGCTTCA 2320       2330       2340       2350       2360       2370       2380
ATCCACCCG CTAAAGTACT TGGACGGGTC TCTCCCTCCC TCATCAGCCC ACCAAACCAA ACCTAGCCTC 2390       2400       2410       2420       2430       2440       2450
CAAGAGTGGG AAGAAATTAA AGCAAGATAG GCTATTAAGT GCAGAGGGAG AGAAAATGCC TCCAACATGT 2460       2470       2480       2490       2500       2510       2520
GAGGAGTAA TGAGAGAAAT CATAGAGAATT CTTCCGCTTC CTGCCTCACT GACTGCCTGC GCTCGGTCGT 2530       2540       2550       2560       2570       2580       2590
TCGGCTGGGG CGAGGGTAT CAGCCTCACTC AAAGCGGTA ATACGTTAT CCACAGAATC AGGGATAAC 2600       2610       2620       2630       2640       2650       2660
GCAGGAAGA ACATGTGAGC AAAGGCCAG CAGCTCACTC AAAGGCCAG GGAACCGTAA AAAGCCCGG TTGCTGGGT 2670       2680       2690       2700       2710       2720       2730
TTTCCATAG GCTCCGCCCC CCTTGACGAGC ATCACAAAAA TCGACGCTCA AGTCAGAGGT GGCGAAACCC
```

FIG. 11F

```
        2740       2750       2760       2770       2780       2790       2800
GACAGGACTA TAAAGATACC AGGGTTTCC CCTGGAAGC TCCCTGGTGC GCTCTCCTGT TCCGACCCTG 2810       2820       2830       2840       2850       2860       2870
CCGCTTACCG GATACCTGTC CGCCTTCTC CCTTCGGGAA GGGTGGGGCT TTCTCATAGC TCAGCTGTA 2880       2890       2900       2910       2920       2930       2940
GGTATCTCAG TTCGGTGTAG GTCGTTCGCT CCAAGCTGGG CTGTGTGCAC GAACCCCCCG TTCAGCCCGA 2950       2960       2970       2980       2990       3000       3010
CCGCTGGGCC TTATCGGTA ACTATCGTCT TGAGTCCAAC CCGGTAAGAC ACGACTTATC GCCACTGGCA 3020       3030       3040       3050       3060       3070       3080
GCAGCCACTG GTAACAGGAT TAGCAGAGCG AGGTATGTAG GCGGTGCTAC AGAGTTCTTG AAGTGGTGGC 3090       3100       3110       3120       3130       3140       3150
CTAACTACGG CTACACTAGA AGAACAGTAT TTGGTATCTG CGCTCTGCTG AAGCCAGTTA CCTTCGGAAA 3160       3170       3180       3190       3200       3210       3220
AAGAGTTGGT AGCTCTTGAT CCGGCAAACA AACCACCGCT GGTAGCGGTG GTTTTTTGT TTGCAAGCAG 3230       3240       3250       3260       3270       3280       3290
CAGATTACGC GCAGAAAAA AGGATCTCAA GAAGATCCTT TGATCTTTTC TACGGGTCT GACGCTCAGT
```

FIG.11G

```
     3300       3310       3320       3330       3340       3350       3360
GGAAGGAAAA CTCAGTTAA GGGATTTGTG TCATGAGATT ATCAAAAAGG ATCTTCACCT AGATCTTTT 3370       3380       3390       3400       3410       3420       3430
AAATTAAAAA TGAAGTTTTA AATCAATCTA AAGTATATAT GAGTAAACTT GTCTGACAG TTACCAATGC 3440       3450       3460       3470       3480       3490       3500
TTAATCAGTG AGGCACCTAT CTCACCGATC TGTCTATTTC GTTCATCCAT AGTTGCCTGA CTCGGGGG 3510       3520       3530       3540       3550       3560       3570
GGGGGCTG AGGTCTGCCT CGTGAAGAAG GTGTTGCTGA CTCATACCAG GCCTGAATCG CCCATCATC 3580       3590       3600       3610       3620       3630       3640
CAGCCAGAAA GTGAGGGAGC CACGGTTGAT GAGACTTG TGTAGTGG ACCAGTTGT GATTTGAAC 3650       3660       3670       3680       3690       3700       3710
TTTTGCTTTG CCACGGAAGG GTCTGGGTTG TCGGAAGAT GCGTGATCTG ATCCTTCAAC TCAGCAAAG 3720       3730       3740       3750       3760       3770       3780
TTCGATTTAT TCAACAAGC CCCGTCCCG TCAAGTCAGC GTAATGCTCT GCCAGTGTTA CAACCAATTA 3790       3800       3810       3820       3830       3840       3850
ACCAATGTG ATTAGAAAAA CTCATCGAGC ATCAAATGAA ACTGCAATTT ATTCATATCA GGATTATCAA
```

FIG.11H

```
      3860       3870       3880       3890       3900       3910       3920
TACCATATATT TTGAAAAAGC CGTTTCTGTA ATGAAGGAGA AAACTCACCG AGGCAGTTCC ATAGGATGGC 3930       3940       3950       3960       3970       3980       3990
AAGATCCTGG TATCGGTCTG CGATTCCGAC TGTCCAACA TCAATACAAC CTATTAATTT CCCTCTGTCA 4000       4010       4020       4030       4040       4050       4060
AAAATAAGT TATCAAGTGA GAAATCACCA TGAGTGACGA CTGAATCCGG TGAGAATGGC AAAAGCTTAT 4070       4080       4090       4100       4110       4120       4130
GCATTTCTT CCTGACTGTC TCAACAGGCC AGCCATTACG CTCGTCATCA AAATCACTCG CATCAACCAA 4140       4150       4160       4170       4180       4190       4200
ACGTTATTC ATTCGTGATT GCGCCTGAGC GAGACGAAAT ACGCGATCGC TGTTAAAAGG ACAATTACAA 4210       4220       4230       4240       4250       4260       4270
ACAGGAATCG AATGCAACCG GCGCAGGAAC ACTGCCAGCG CATCAACAAT ATTTTCACCT GAATCAGGAT 4280       4290       4300       4310       4320       4330       4340
ATTCTTCTAA TACCTGGAAT GCTGTTTTCC CGGGGATCGC AGTGGTGAGT AACCATGCAT CATCAGGAGT 4350       4360       4370       4380       4390       4400       4410
ACGGATAAAA TGCTTGATGG TCGGAAGAGG CATAAATTCC GTCAGCCAGT TTAGTCTGAC CATCTCATCT
```

FIG.11I

```
        4420       4430       4440       4450       4460       4470       4480
GTAACATCAT TGGCAACGCT ACCTTGCCA TGTTTCAGAA ACAACTCTGG CCGATGGGC TTCCATACA 4490       4500       4510       4520       4530       4540       4550
ATCGATAGAT TGTCGACCT GATTGCCCGA CATTATGCGG AGCCATTTA TACCCATATA AATCAGCATC 4560       4570       4580       4590       4600       4610       4620
CATGTTGGAA TTTAATGCGG GCCTCGAGCA AGAGTTTCC CGTTGAATAT GGCTCATAAC GTTCCTGTA 4630       4640       4650       4660       4670       4680       4690
TTACTGTTTA TGTAAGCAGA CAGTTTTATT GTTCATGATG ATATATTTTT ATCTTGTGCA ATGTAACATC 4700       4710       4720       4730       4740       4750       4760
AGAGATTTTG AGACACAAG TGGCTTTCCC CCCCCCCCCA TTATTGAAGC ATTATCAGG GTTATTGTCT 4770       4780       4790       4800       4810       4820       4830
CATGACGGA TACATATTTG AATGTATTTA GAAAAATAAA CAAATAGGGG TTCCGGCCAC ATTTCCCGA 4840       4850       4860       4870       4880       4890       4900
AAAGTGCCAC CTGACGTCTA AGAAACCATT ATTATCATGA CATTAACCTA TAAAAATAGG CGTATCACGA

4910
GGCCCTTTCG TC
```

FIG. 12

5' AAG CTT CAG GAA CGA CCA ACT ACC CCG ATC ATC AGT TAT CCT
TAA GGT CTC TTT TGT GTG GTG CGT TCC GGT ATG GGG GGG ACT GCC
                                                     Met Gly Gly Thr Ala
GCC AGG TTG GGG GCC GTG ATT TTG TTT GTC GTC ATA GTG GGC CTC
Ala Arg Leu Gly Ala Val Ile Leu Phe Val Val Ile Val Gly Leu
CAT GGG GTC CGC GGC AAA TAT GCC TTG GCG GAT GCC TCT CTC 3'
His Gly Val Arg Gly Lys Tyr Ala Leu Ala Asp Ala Ser Leu

SEQUENCE LISTING (1) GENERAL INFORMATION:

(iii) NUMBER OF SEQUENCES: 5

(2) INFORMATION FOR SEQ ID NO:1:

(i) SEQUENCE CHARACTERISTICS:
      (A) LENGTH: 1886 base pairs
      (B) TYPE: nucleic acid
      (C) STRANDEDNESS: single
      (D) TOPOLOGY: linear (xi) SEQUENCE DESCRIPTION: SEQ ID NO:1:

```
ATGGAGTTGC CAATCCTCAA AGCAAATGCA ATTACCACAA TCCTCGCTGC AGTCACATTT      60

TGCTTTGCTT CTAGTCAAAA CATCACTGAA GAATTTTATC AATCAACATG CAGTGCAGTT     120

AGCAAAGGCT ATCTTAGTGC TCTAAGAACT GGTTGGTATA CTAGTGTTAT AACTATAGAA     180

TTAAGTAATA TCAAGGAAAA TAAGTGTAAT GGAACAGATG CTAAGGTAAA ATTGATGAAA     240

CAAGAATTAG ATAAATATAA AAATGCTGTA ACAGAATTGC AGTTGCTCAT GCAAAGCACA     300

CCAGCAGCAA ACAATCGAGC CAGAAGAGAA CTACCAAGGT TTATGAATTA TACACTCAAC     360

AATACCAAAA AAACCAATGT AACATTAAGC AAGAAAAGGA AAAGAAGATT TCTTGGTTTT     420

TTGTTAGGTG TTGGATCTGC AATCGCCAGT GGCATTGCTG TATCTAAGGT CCTGCACTTA     480

GAAGGAGAAG TGAACAAGAT CAAAAGTGCT CTACTATCCA CAAACAAGGC CGTAGTCAGC     540

TTATCAAATG GAGTTAGTGT CTTAACCAGC AAAGTGTTAG ACCTCAAAAA CTATATAGAT     600

AAACAATTGT TACCTATTGT GAATAAGCAA AGCTGCAGAA TATCAAATAT AGAAACTGTG     660

ATAGAGTTCC AACAAAAGAA CAACAGACTA CTAGAGATTA CCAGGGAATT TAGTGTTAAT     720

GCAGGTGTAA CTACACCTGT AAGCACTTAC ATGTTAACTA ATAGTGAATT ATTGTCATTA     780

ATCAATGATA TGCCTATAAC AAATGATCAG AAAAAGTTAA TGTCCAACAA TGTTCAAATA     840

GTTAGACAGC AAAGTTACTC TATCATGTCC ATAATAAAAG AGGAAGTCTT AGCATATGTA     900

GTACAATTAC CACTATATGG TGTGATAGAT ACACCTTGTT GGAAATTACA CACATCCCCT     960

CTATGTACAA CCAACACAAA AGAAGGGTCA AACATCTGTT TAACAAGAAC TGACAGAGGA    1020

TGGTACTGTG ACAATGCAGG ATCAGTATCT TTCTTCCCAC AAGCTGAAAC ATGTAAAGTT    1080

CAATCGAATC GAGTATTTTG TGACACAATG AACAGTTTAA CATTACCAAG TGAAGTAAAT    1140

CTCTGCAATG TTGACATATT CAATCCCAAA TATGATTGTA AAATTATGAC TTCAAAAACA    1200

GATGTAAGCA GCTCCGTTAT CACATCTCTA GGAGCCATTG TGTCATGCTA TGGCAAAACT    1260

AAATGTACAG CATCCAATAA AAATCGTGGA ATCATAAAGA CATTTTCTAA CGGGTGTGAT    1320

TATGTATCAA ATAAAGGGGT GGACACTGTG TCTGTAGGTA ACACATTATA TTATGTAAAT    1380

AAGCAAGAAG GCAAAAGTCT CTATGTAAAA GGTGAACCAA TAATAAATTT CTATGACCCA    1440

TTAGTATTCC CCTCTGATGA ATTTGATGCA TCAATATCTC AAGTCAATGA GAAGATTAAC    1500

CAGAGTTTAG CATTTATTCG TAAATCCGAT GAATTATTAC ATAATGTAAA TGCTGGTAAA    1560

TCAACCACAA ATATCATGAT AACTACTATA ATTATAGTGA TTATAGTAAT ATTGTTATCA    1620

TTAATTGCTG TTGGACTGCT CCTATACTGT AAGGCCAGAA GCACACCAGT CACACTAAGC    1680

AAGGATCAAC TGAGTGGTAT AAATAATATT GCATTTAGTA ACTGAATAAA AATAGCACCT    1740
```

```
AATCATGTTC TTACAATGGT TTACTATCTG CTCATAGACA ACCCATCTAT CATTGGATTT    1800

TCTTAAAATC TGAACTTCAT CGAAACTCTT ATCTATAAAC CATCTCACTT ACACTATTTA    1860

AGTAGATTCC TAGTTTATAG TTATAT                                         1886
```

(2) INFORMATION FOR SEQ ID NO:2:

(i) SEQUENCE CHARACTERISTICS:
        (A) LENGTH: 594 amino acids
        (B) TYPE: amino acid
        (C) STRANDEDNESS: single
        (D) TOPOLOGY: linear (xi) SEQUENCE DESCRIPTION: SEQ ID NO:2:

```
Met Glu Leu Pro Ile Leu Lys Ala Asn Ala Ile Thr Thr Ile Leu Ala
1               5                   10                  15

Ala Val Thr Phe Cys Phe Ala Ser Ser Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Met Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Ala Asn Asn Arg Ala Arg Arg Glu Leu Pro
            100                 105                 110

Arg Phe Met Asn Tyr Thr Leu Asn Asn Thr Lys Lys Thr Asn Val Thr
        115                 120                 125

Leu Ser Lys Lys Arg Lys Arg Arg Phe Leu Gly Phe Leu Leu Gly Val
    130                 135                 140

Gly Ser Ala Ile Ala Ser Gly Ile Ala Val Ser Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Ser Lys Val
            180                 185                 190

Leu Asp Leu Lys Asn Tyr Ile Asp Lys Gln Leu Leu Pro Ile Val Asn
        195                 200                 205

Lys Arg Ser Cys Arg Ile Ser Asn Ile Glu Thr Val Ile Glu Phe Gln
    210                 215                 220

His Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Asn Asn Val Gln Ile Val Arg Gln Gln Ser Tyr Ser Ile
        275                 280                 285

Met Ser Ile Ile Lys Glu Glu Val Leu Ala Tyr Val Val Gln Leu Pro
    290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
```

```
                     325                 330                 335
Thr Asp Arg Gly Trp Tyr Cys Asp Asn Ala Gly Ser Val Ser Phe Phe
                340                 345                 350

Pro Gln Ala Glu Thr Cys Lys Val Gln Ser Asn Arg Val Phe Cys Asp
            355                 360                 365

Thr Met Asn Ser Leu Thr Leu Pro Ser Glu Val Asn Leu Cys Asn Val
        370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
                420                 425                 430

Lys Thr Phe Ser Asn Gly Cys Asp Tyr Val Ser Asn Lys Gly Val Asp
            435                 440                 445

Thr Val Ser Val Gly Asn Thr Leu Tyr Tyr Val Asn Lys Gln Glu Gly
        450                 455                 460

Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Leu Val Phe Pro Ser Asp Glu Phe Asp Ala Ser Ile
                500                 505                 510

Ser Gln Val Asn Glu Lys Ile Asn Gln Ser Leu Ala Phe Ile Arg Lys
            515                 520                 525

Ser Asp Glu Leu Leu His Asn Val Asn Ala Gly Lys Ser Thr Thr Asn
        530                 535                 540

Ile Met Ile Thr Thr Ile Ile Ile Glu Ile Ile Val Ile Leu Leu Ser
545                 550                 555                 560

Leu Ile Ala Val Gly Leu Leu Leu Tyr Cys Lys Ala Arg Ser Thr Pro
                565                 570                 575

Val Thr Leu Ser Lys Asp Gln Leu Ser Gly Ile Asn Asn Ile Ala Phe
            580                 585                 590

Ser Asn (2) INFORMATION FOR SEQ ID NO:3:

(i) SEQUENCE CHARACTERISTICS:
        (A) LENGTH: 1904 base pairs
        (B) TYPE: nucleic acid
        (C) STRANDEDNESS: single
        (D) TOPOLOGY: linear (xi) SEQUENCE DESCRIPTION: SEQ ID NO:3:

ATGGAGTTGC CAATCCTCAA AGCAAATGCA ATTACCACAA TCCTCGCTGC AGTCACATTT      60

TGCTTTGCTT CTAGTCAAAA CATCACTGAA GAATTTTATC AATCAACATG CAGTGCAGTT    120

AGCAAAGGCT ATCTTAGTGC TCTAAGAACT GGTTGGTATA CTAGTGTTAT AACTATAGAA    180

TTAAGTAATA TCAAGGAAAA TAAGTGTAAT GGAACAGATG CTAAGGTAAA ATTGATGAAA    240

CAAGAATTAG ATAAATATAA AAATGCTGTA ACAGAATTGC AGTTGCTCAT GCAAAGCACA    300

CCAGCAGCAA ACAATCGAGC CAGAAGAGAA CTACCAAGGT TTATGAATTA TACACTCAAC    360

AATACCAAAA AAACCAATGT AACATTAAGC AAGAAAAGGA AAAGAAGATT CTTGGTTTTT    420

TTGTTAGGTG TTGGATCTGC AATCGCCAGT GGCATTGCTG TATCTAAGGT CCTGCACTTA    480
```

```
GAAGGAGAAG TGAACAAGAT CAAAAGTGCT CTACTATCCA CAAACAAGGC CGTAGTCAGC     540

TTATCAAATG GAGTTAGTGT CTTAACCAGC AAAGTGTTAG ACCTCAAAAA CTATATAGAT     600

AAACAATTGT TACCTATTGT GAATAAGCAA AGCTGCAGAA TATCAAATAT AGAAACTGTG     660

ATAGAGTTCC AACAAAGAA CAACAGACTA CTAGAGATTA CCAGGGAATT TAGTGTTAAT     720

GCAGGTGTAA CTACACCTGT AAGCACTTAC ATGTTAACTA ATAGTGAATT ATTGTCATTA     780

ATCAATGATA TGCCTATAAC AAATGATCAG AAAAAGTTAA TGTCCAACAA TGTTCAAATA     840

GTTAGACAGC AAAGTTACTC TATCATGTCC ATAATAAAAG AGGAAGTCTT AGCATATGTA     900

GTACAATTAC CACTATATGG TGTGATAGAT ACACCTTGTT GGAAATTACA CACATCCCCT     960

CTATGTACAA CCAACACAAA AGAAGGGTCA ACATCTGTT TAACAAGAAC TGACAGAGGA    1020

TGGTACTGTG ACAATGCAGG ATCAGTATCT TTCTTCCCAC AAGCTGAAAC ATGTAAAGTT    1080

CAATCGAATC GAGTATTTTG TGACACAATG AACAGTTTAA CATTACCAAG TGAAGTAAAT    1140

CTCTGCAATG TTGACATATT CAATCCCAAA TATGATTGTA AAATTATGAC TTCAAAAACA    1200

GATGTAAGCA GCTCCGTTAT CACATCTCTA GGAGCCATTG TGTCATGCTA TGGCAAAACT    1260

AAATGTACAG CATCCAATAA AAATCGTGGA ATCATAAAGA CATTTTCTAA CGGGTGTGAT    1320

TATGTATCAA ATAAAGGGGT GGACACTGTG TCTGTAGGTA ACACATTATA TTATGTAAAT    1380

AAGCAAGAAG GCAAAAGTCT CTATGTAAAA GGTGAACCAA TAATAAATTT CTATGACCCA    1440

TTAGTATTCC CCTCTGATGA ATTTGATGCA TCAATATCTC AAGTCAATGA GAAGATTAAC    1500

CAGAGTTTAG CATTTATTCG TAAATCCGAT GAATTATTAC ATAATGTAAA TGCTGGTAAA    1560

TCAACCACAA ATATCATGAC TTGATAATGA GGATCCATAA CTACTATAAT TATAGTGATT    1620

ATAGTAATAT TGTTATCATT AATTGCTGTT GGACTGCTCC TATACTGTAA GGCCAGAAGC    1680

ACACCAGTCA CACTAAGCAA GGATCAACTG AGTGGTATAA ATAATATTGC ATTTAGTAAC    1740

TGAATAAAAA TAGCACCTAA TCATGTTCTT ACAATGGTTT ACTATCTGCT CATAGACAAC    1800

CCATCTATCA TTGGATTTTC TTAAAATCTG AACTTCATCG AAACTCTTAT CTATAAACCA    1860

TCTCACTTAC ACTATTTAAG TAGATTCCTA GTTTATAGTT ATAT                     1904
```

(2) INFORMATION FOR SEQ ID NO:4:

(i) SEQUENCE CHARACTERISTICS:
        (A) LENGTH: 527 amino acids
        (B) TYPE: amino acid
        (C) STRANDEDNESS: single
        (D) TOPOLOGY: linear (xi) SEQUENCE DESCRIPTION: SEQ ID NO:4:

```
Met Glu Leu Pro Ile Leu Lys Ala Asn Ala Ile Thr Thr Ile Leu Ala
1               5                   10                  15

Ala Val Thr Phe Cys Phe Ala Ser Ser Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Met Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Ala Asn Asn Arg Ala Arg Arg Glu Leu Pro
            100                 105                 110
```

-continued

```
Arg Phe Met Asn Tyr Thr Leu Asn Thr Lys Lys Thr Asn Val Thr
            115                 120                 125
Leu Ser Lys Lys Arg Lys Arg Arg Phe Leu Gly Phe Leu Leu Gly Val
    130                 135                 140
Gly Ser Ala Ile Ala Ser Gly Ile Ala Val Ser Lys Val Leu His Leu
145                 150                 155                 160
Glu Gly Glu Val Asn Lys Ile Lys Ser Ala Leu Leu Ser Thr Asn Lys
                    165                 170                 175
Ala Val Val Ser Leu Ser Asn Gly Val Ser Val Leu Thr Ser Lys Val
            180                 185                 190
Leu Asp Leu Lys Asn Tyr Ile Asp Lys Gln Leu Leu Pro Ile Val Asn
        195                 200                 205
Lys Gln Ser Cys Arg Ile Ser Asn Ile Glu Thr Val Ile Glu Phe Gln
    210                 215                 220
His Lys Asn Asn Arg Leu Leu Glu Ile Thr Arg Glu Phe Ser Val Asn
225                 230                 235                 240
Ala Gly Val Thr Thr Pro Val Ser Thr Tyr Met Leu Thr Asn Ser Glu
                245                 250                 255
Leu Leu Ser Leu Ile Asn Asp Met Pro Ile Thr Asn Asp Gln Lys Lys
            260                 265                 270
Leu Met Ser Asn Asn Val Gln Ile Val Arg Gln Gln Ser Tyr Ser Ile
        275                 280                 285
Met Ser Ile Ile Lys Glu Glu Val Leu Ala Tyr Val Val Gln Leu Pro
    290                 295                 300
Leu Tyr Gly Val Ile Asp Thr Pro Cys Trp Lys Leu His Thr Ser Pro
305                 310                 315                 320
Leu Cys Thr Thr Asn Thr Lys Glu Gly Ser Asn Ile Cys Leu Thr Arg
                325                 330                 335
Thr Asp Arg Gly Trp Tyr Cys Asp Asn Ala Gly Ser Val Ser Phe Phe
            340                 345                 350
Pro Gln Ala Glu Thr Cys Lys Val Gln Ser Asn Arg Val Phe Cys Asp
        355                 360                 365
Thr Met Asn Ser Leu Thr Leu Pro Ser Glu Val Asn Leu Cys Asn Val
    370                 375                 380
Asp Ile Phe Asn Pro Lys Tyr Asp Cys Lys Ile Met Thr Ser Lys Thr
385                 390                 395                 400
Asp Val Ser Ser Ser Val Ile Thr Ser Leu Gly Ala Ile Val Ser Cys
                405                 410                 415
Tyr Gly Lys Thr Lys Cys Thr Ala Ser Asn Lys Asn Arg Gly Ile Ile
            420                 425                 430
Lys Thr Phe Ser Asn Gly Cys Asp Tyr Val Ser Asn Lys Gly Val Asp
        435                 440                 445
Thr Val Ser Val Gly Asn Thr Leu Tyr Tyr Val Asn Lys Gln Glu Gly
    450                 455                 460
Lys Ser Leu Tyr Val Lys Gly Glu Pro Ile Ile Asn Phe Tyr Asp Pro
465                 470                 475                 480
Leu Val Phe Pro Ser Asp Glu Phe Asp Ala Ser Ile Ser Gln Val Asn
                485                 490                 495
Glu Lys Ile Asn Gln Ser Leu Ala Phe Ile Arg Lys Ser Asp Glu Leu
            500                 505                 510
Leu His Asn Val Asn Ala Gly Lys Ser Thr Thr Asn Ile Met Thr
        515                 520                 525
```

-continued

```
(2) INFORMATION FOR SEQ ID NO:5:

(i) SEQUENCE CHARACTERISTICS:
         (A) LENGTH: 573 base pairs
         (B) TYPE: nucleic acid
         (C) STRANDEDNESS: single
         (D) TOPOLOGY: linear (xi) SEQUENCE DESCRIPTION: SEQ ID NO:5:

GTGAGTTTGG GGACCCTTGA TTGTTCTTTC TTTTTCGCTA TTGTAAAATT CATGTTATAT     60

GGAGGGGGCA AAGTTTTCAG GGTGTTGTTT AGAATGGGAA GATGTCCCTT GTATCACCAT    120

GGACCCTCAT GATAATTTTG TTTCTTTCAC TTTCTACTCT GTTGACAACC ATTGTCTCCT    180

CTTATTTTCT TTTCATTTTC TGTAACTTTT TCGTTAAACT TTAGCTTGCA TTTGTAACGA    240

ATTTTTAAAT TCACTTTTGT TTATTTGTCA GATTGTAAGT ACTTTCTCTA ATCACTTTTT    300

TTTCAAGGCA ATCAGGGTAT ATTATATTGT ACTTCAGCAC AGTTTTAGAG AACAATTGTT    360

ATAATTAAAT GATAAGGTAG AATATTTCTG CATATAAATT CTGGCTGGCG TGGAAATATT    420

CTTATTGGTA GAAACAACTA CATCCTGGTC ATCATCCTGC CTTTCTCTTT ATGGTTACAA    480

TGATATACAC TGTTTGAGAT GAGGATAAAA TACTCTGAGT CCAAACCGGG CCCCTCTGCT    540

AACCATGTTC ATGCCTTCTT CTTTTTCCTA CAG                                 573
```

NUCLEIC ACID RESPIRATORY SYNCYTIAL VIRUS VACCINES

REFERENCE TO RELATED APPLICATIONS

This application is a continuation-in-part of U.S. application Ser. No. 08/896,500 filed Jul. 18, 1997 (now U.S. Pat. No. 6,017,897), which itself is a continuation-in-part of U.S. patent application Ser. No. 08/659,939 filed Jun. 7, 1996 (now U.S. Pat. No. 5,843,913), which itself is continuation-in-part of U.S. patent application Ser. No. 08/476,397, filed Jun. 7, 1995 (now U.S. Pat. No. 6,019,980).

FIELD OF INVENTION

The present invention is related to the field of Respiratory Syncytial Virus (RSV) vaccines and is particularly concerned with vaccines comprising nucleic acid sequences encoding the fusion (F) protein of RSV.

BACKGROUND OF INVENTION

Respiratory syncytial virus (RSV), a negative-strand RNA virus belonging to the Paramyxoviridae family of viruses, is the major viral pathogen responsible for bronchiolitis and pneumonia in infants and young children (ref. 1—Throughout this application, various references are referred to in parenthesis to more fully describe the state of the art to which this invention pertains. Full bibliographic information for each citation is found at the end of the specification, immediately preceding the claims. The disclosures of these references are hereby incorporated by reference into the present disclosure). Acute respiratory tract infections caused by RSV result in approximately 90,000 hospitalizations and 4,500 deaths per year in the United States (ref. 2). Medical care costs due to RSV infection are greater than $340 M annually in the United States alone (ref. 3). There is currently no licensed vaccine against RSV. The main approaches for developing an RSV vaccine have included inactivated virus, live-attenuated viruses and subunit vaccines.

The F protein of RSV is considered to be one of the most important protective antigens of the virus. There is a significant similarity (89% identity) in the amino acid sequences of the F proteins from RSV subgroups A and B (ref. 3) and anti-F antibodies can cross-neutralize viruses of both subgroups as well as protect immunized animals against infection with viruses from both subgroups (ref. 4). Furthermore, the F protein has been identified as a major target for RSV-specific cytotoxic T-lymphocytes in mice and humans (ref. 3 and ref. 5).

The use of RSV proteins as vaccines may have obstacles. Parenterally administered vaccine candidates have so far proven to be poorly immunogenic with regard to the induction of neutralizing antibodies in seronegative humans or chimpanzees. The serum antibody response induced by these antigens may be further diminished in the presence of passively acquired antibodies, such as the transplacentally acquired maternal antibodies which most young infants possess. A subunit vaccine candidate for RSV consisting of purified fusion glycoprotein from RSV infected cell cultures and purified by immunoaffinity or ion-exchange chromatography has been described (ref. 6). Parenteral immunization of seronegative or seropositive chimpanzees with this preparation was performed and three doses of 50 μg were required in seronegative animals to induce an RSV serum neutralizing titre of approximately 1:50. Upon subsequent challenge of these animals with wild-type RSV, no effect of immunization on virus shedding or clinical disease could be detected in the upper respiratory tract. The effect of immunization with this vaccine on virus shedding in the lower respiratory tract was not investigated, although this is the site where the serum antibody induced by parenteral immunization may be expected to have its greatest effect. Safety and immunogenicity studies have been performed in a small number of seropositive individuals. The vaccine was found to be safe in seropositive children and in three seronegative children (all >2.4 years of age). The effects of immunization on lower respiratory tract disease could not be determined because of the small number of children immunized. One immunizing dose in seropositive children induced a 4-fold increase in virus neutralizing antibody titres in 40 to 60% of the vaccinees. Thus, insufficient information is available from these small studies to evaluate the efficacy of this vaccine against RSV-induced disease. A further problem facing subunit RSV vaccines is the possibility that inoculation of seronegative subjects with immunogenic preparations might result in disease enhancement (sometimes referred to as immunopotentiation) similar to that seen in formalin inactivated RSV vaccines. In some studies, the immune response to immunization with RSV F protein or a synthetic RSV FG fusion protein resulted in a disease enhancement in rodents resembling that induced by a formalin-inactivated RSV vaccine. The association of immunization with disease enhancement using non-replicating antigens suggests caution in their use as vaccines in seronegative humans.

Live attenuated vaccines against disease caused by RSV may be promising for two main reasons. Firstly, infection by a live vaccine virus induces a balanced immune response comprising mucosal and serum antibodies and cytotoxic T-lymphocytes. Secondly, infection of infants with live attenuated vaccine candidates or naturally acquired wild-type virus is not associated with enhanced disease upon subsequent natural reinfection. It will be challenging to produce live attenuated vaccines that are immunogenic for younger infants who possess maternal virus-neutralizing antibodies and yet are attenuated for seronegative infants greater than or equal to 6 months of age. Attenuated live virus vaccines also have the risks of residual virulence and genetic instability.

Injection of plasmid DNA containing sequences encoding a foreign protein has been shown to result in expression of the foreign protein and the induction of antibody and cytotoxic T-lymphocyte responses to the antigen in a number of studies (see, for example, refs. 7, 8, 9). The use of plasmid DNA inoculation to express viral proteins for the purpose of immunization may offer several advantages over the strategies summarized above. Firstly, DNA encoding a viral antigen can be introduced in the presence of antibody to the virus itself, without loss of potency due to neutralization of virus by the antibodies. Secondly, the antigen expressed in vivo should exhibit a native conformation and, therefore, should induce an antibody response similar to that induced by the antigen present in the wild-type virus infection. In contrast, some processes used in purification of proteins can induce conformational changes which may result in the loss of immunogenicity of protective epitopes and possibly immunopotentiation.

Thirdly, the expression of proteins from injected plasmid DNAs can be detected in vivo for a considerably longer period of time than that in virus-infected cells, and this has the theoretical advantage of prolonged cytotoxic T-cell induction and enhanced antibody responses. Fourthly, in vivo expression of antigen may provide protection without the need for an extrinsic adjuvant.

The ability to immunize against disease caused by RSV by administration of a DNA molecule encoding an RSV F protein was unknown before the present invention. In particular, the efficacy of immunization against RSV induced disease using a gene encoding a secreted form of the RSV F protein was unknown. Infection with RSV leads to serious disease. It would be useful and desirable to provide isolated genes encoding RSV F protein and vectors for in vivo administration for use in immunogenic preparations, including vaccines, for protection against disease caused by RSV and for the generation of diagnostic reagents and kits. In particular, it would be desirable to provide vaccines that are immunogenic and protective in humans, including seronegative infants, that do not cause disease enhancement (immunopotentiation).

SUMMARY OF INVENTION

The present invention relates to a method of immunizing a host against disease caused by respiratory syncytial virus, to nucleic acid molecules used therein, and to diagnostic procedures utilizing the nucleic acid molecules. In particular, the present invention is directed towards the provision of nucleic acid respiratory syncytial virus vaccines.

In accordance with one aspect of the invention, there is provided an immunogenic composition for in vivo administration to a host for the generation in the host of a protective immune response to RSV F protein, comprising a non-replicating vector comprising:

a first nucleotide sequence encoding an RSV F protein or a RSV F protein fragment that generates antibodies and/or cytotoxic T-lymphocytes (CTLs) that specifically react with RSV F protein;

a promoter sequence operatively coupled to the first nucleotide sequence for expression of the RSV F protein, and a second nucleotide sequence located adjacent the first nucleotide sequence to enhance the immunoprotective ability of the RSV F protein when expressed in vivo from the vector in a host; and a pharmaceutically-acceptable carrier therefor.

The first nucleotide sequence may be that which encodes a full-length RSV F protein, as seen in FIG. 2 (SEQ ID No: 2). Alternatively, the first nucleotide sequence may be that which encodes an RSV F protein from which the transmembrane region is absent. The latter embodiment may be provided by a nucleotide sequence which encodes a full-length RSV F protein but contains a translational stop codon immediately upstream of the start of the transmembrane coding region, thereby preventing expression of a transmembrane region of the RSV F protein, as seen in FIG. 3 (SEQ. ID No. 4). The lack of expression of the transmembrane region results in a secreted form of the RSV F protein.

The first nucleotide sequence may encode a RSV F protein fragment lacking an autologous RSV F signal peptide sequence and may include, in its place, a sequence encoding a heterologous signal peptide sequence which enhances the level of expression of the RSV F protein. One signal peptide which has been found useful in this regard is the signal peptide of Herpes Simplex Virus I (HSV I)gD. Such enhanced expression levels also lead to improve immunogenicity of the vector at the same dosage level. The first nucleotide sequence may also encode a RSV F protein fragment lacking a transmembrane coding region.

The second nucleotide sequence may comprise a pair of splice sites to prevent aberrant mRNA splicing, whereby substantially all transcribed mRNA encodes the RSV protein. Such second nucleotide sequence may be located between the first nucleotide sequence and the promoter sequence. Such second nucleotide sequence may be that of rabbit β-globin intron II, as shown in FIG. 8 (SEQ ID No: 5).

A vector encoding the F protein and provided by this aspect of the invention may specifically be pXL2 or pXL4 or p82M35B, as seen in FIGS. 5, 7 or 10, respectively.

The promoter sequence may be an immediate early cytomegalovirus (CMV) promoter.

Certain of the vectors provided herein may be used to immunize a host against RSV infection or disease by in vivo expression of RSV F protein lacking a transmembrane region following administration of the vectors. In accordance with a further aspect of the present invention, therefore, there is provided a method of immunizing a host against disease caused by infection with respiratory syncytial virus, which comprises administering to the host an effective amount a of non-replicating vector comprising a first nucleotide sequence encoding an RSV F protein or a RSV F protein fragment that generates antibodies and/or CTLs that specifically react with RSV F protein and a promoter sequence operatively coupled to the first nucleotide sequence for expression of the RSV F protein in the host, which may be a human. The promoter may be an immediate early cytomegalovirus promoter.

The nucleotide sequence may encode a truncated RSV F protein lacking the transmembrane region may be that as described above and/or possess a heterologous signal peptide encoding sequence.

The vector may contain a second nucleotide sequence located adjacent a first nucleotide sequence and effective to enhance the immunoprotective ability of the RSV F protein expressed by the first nucleotide sequence may be used to immunize a host. Specific non-replicating vectors which may be used in this aspect of the invention are those identified as plasmid vectors pXL2, pXL4 and p82M35B in FIGS. 5, 7 and 10 respectively.

The present invention also includes a novel method of using a gene encoding an RSV F protein or a RSV F protein fragment that generates antibodies and/or CTLs that specifically react with RSV F protein to protect a host against disease caused by infection with respiratory syncytial virus, which comprises:

isolating the gene;

operatively linking the gene to at least one control sequence to produce a non-replicating vector, said control sequence directing expression of the RSV F protein when said vector is introduced into a host to produce an immune response to the RSV F protein or fragment thereof, and introducing the vector into the host.

The procedure provided in accordance with this aspect of the invention may further include the step of:

operatively linking the gene to an immunoprotection enhancing sequence to produce an enhanced immunoprotection by the RSV F protein in the host, preferably by introducing the immunoprotection enhancing sequence between the control sequence and the gene.

In addition, the present invention includes a method of producing a vaccine for protection of a host against disease caused by infection with respiratory syncytial virus, which comprises:

isolating a first nucleotide sequence encoding an RSV F protein or a RSV F protein fragment that generates antibodies and/or CLTs that specifically react with RSV F protein;

operatively linking the first nucleotide sequence to at least one control sequence to produce a non-replicating vector, the control sequence directing expression of the RSV F protein when introduced into a host to produce an immune response to the RSV F protein when expressed in vivo from the vector in a host, and formulating the vector as a vaccine for in vivo administration.

The first nucleotide sequence further may be operatively linked to a second nucleotide sequence to enhance the immunoprotective ability of the RSV F protein when expressed in vivo from the vector in a host. The vector may be a plasmid vector selected from pXL2, pXL4 and p82M35B. The invention further includes a vaccine for administration to a host, including a human host, produced by this method as well as immunogenic compositions comprising an immunoeffective amount of the vectors described herein.

As noted previously, the vectors provided herein are useful in diagnostic applications. In a further aspect of the invention, therefore, there is provided a method of determining the presence of an RSV F protein in a sample, comprising the steps of:

(a) immunizing a host with a non-replicating vector comprising a first nucleotide sequence encoding an RSV F protein or a RSV F protein fragment that generates antibodies and/or cytotoxic T-lymphocytes (CTLs) that specifically react with RSV F protein and a promoter sequence operatively coupled to the first nucleotide sequence for expression of the RSV F protein in the host to produce antibodies specific for the RSV F protein;

(b) isolating the RSV F protein specific antibodies;

(c) contacting the sample with the isolated antibodies to produce complexes comprising any RSV F protein present in the sample and the RSV F protein-specific antibodies; and (d) determining production of the complexes.

The non-replicating vector employed to elicit the antibodies may be a plasmid vector which is pXL1, pXL2, pXL3, pXL4 or p82M35B.

The invention also includes a diagnostic kit for detecting the presence of an RSV F protein in a sample, comprising:

(a) a non-replicating vector comprising a first nucleotide sequence encoding an RSV F protein or a RSV F protein fragment that generates antibodies that specifically react with RSV F protein and a promoter sequence operatively coupled to said first nucleotide sequence for expression of said RSV F protein in a host immunized therewith to produce antibodies specific for the RSV F protein;

(b) isolation means to isolate said RSV F protein specific antibodies;

(c) contacting means to contact the isolated RSV F specific antibodies with the sample to produce a complex comprising any RSV F protein present in the sample and RSV F protein specific antibodies; and (d) identifying means to determine production of the complex.

The present invention is further directed to a method for producing RSV F protein specific polyclonal antibodies comprising the use of the immunization method described herein, and further comprising the step of isolating the RSV F protein specific polyclonal antibodies from the immunized animal.

The present invention is also directed to a method for producing monoclonal antibodies specific for an F protein of RSV, comprising the steps of:

(a) constructing a non-replicating vector comprising a first nucleotide sequence encoding a RSV F protein and a promoter sequence operatively coupled to said first nucleotide sequence for expression of said RSV F protein; and, optionally, a second nucleotide sequence located adjacent said first nucleotide sequence to enhance the immunoprotective ability of said RSV F protein when expressed in vivo from said vector in a host.

(b) administering the vector to at least one mouse to produce at least one immunized mouse;

(c) removing B-lymphocytes from the at least one immunized mouse;

(d) fusing the B-lymphocytes from the at least one immunized mouse with myeloma cells, thereby producing hybridomas;

(e) cloning the hybridomas;

(f) selecting clones which produce anti-F protein antibody;

(g) culturing the anti-F protein antibody-producing clones; and (h) isolating anti-F protein monoclonal antibodies.

In this application, the term "RSV F protein" is used to define (1) a full-length RSV F protein, such proteins having variations in their amino acid sequences including those naturally occurring in various strains of RSV, (2) a secreted form of RSV F protein lacking a transmembrane region, and (3) functional analogs of the RSV F protein. In this application, a first protein is a "functional analog" of a second protein if the first protein is immunologically related to and/or has the same function as the second protein. The functional analog may be, for example, a fragment of the protein or a substitution, addition or deletion mutant thereof. Included are RSV F protein fragments that generate antibodies and/or CTLs that specifically react with RSV F protein.

BRIEF DESCRIPTION OF THE FIGURES

The present invention will be further understood from the following General Description and Examples with reference to the Figures in which:

FIGS. 2A, 2B, 2C, 2D and 2E show the nucleotide sequence of the gene encoding the membrane attached form of the F protein of Respiratory Syncytial Virus (SEQ ID No: 1) as well as the amino acid sequence of the RSV F protein encoded thereby (SEQ ID No: 2);

FIGS. 3A, 3B, 3C and 3D show the nucleotide sequence of the gene encoding the secreted form of the RSV F protein lacking the transmembrane region (SEQ ID No: 3) as well as the amino acid sequence of the truncated RSV F protein lacking the transmembrane region encoded thereby (SEQ ID No: 4);

FIG. 8 shows the nucleotide sequence for the rabbit β-globin Intron II sequence (SEQ ID No. 5);

FIG. 11 shows the nucleotide sequence of plasmid VR-1012 (SEQ ID No: 6); and

FIG. 12 shows DNA (SEQ ID No: 7) and derived amino acid (SEQ ID No: 8) sequence of the HSV gD signal peptide sequence, synthesized as a synthetic oligopeptide.

GENERAL DESCRIPTION OF INVENTION

Figure 1:
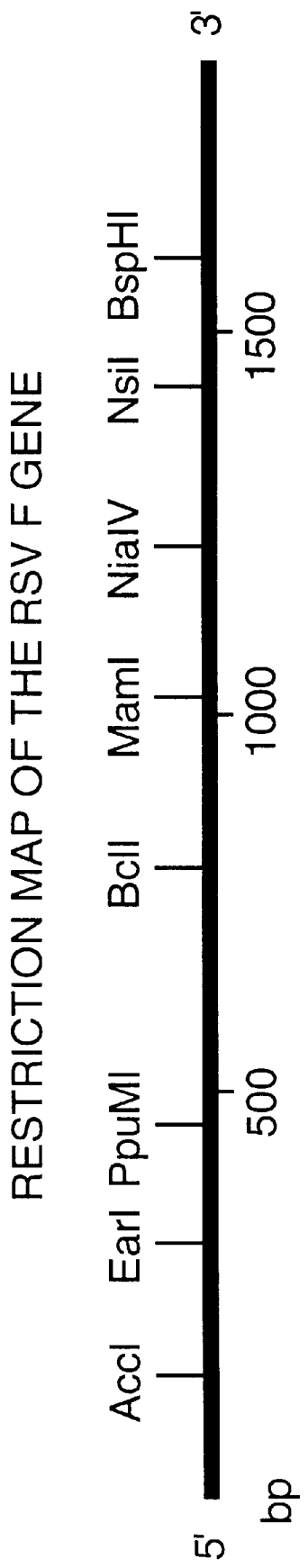
FIG. 1 illustrates a restriction map of the gene encoding the F protein of Respiratory Syncytial Virus.
Figure 4A:
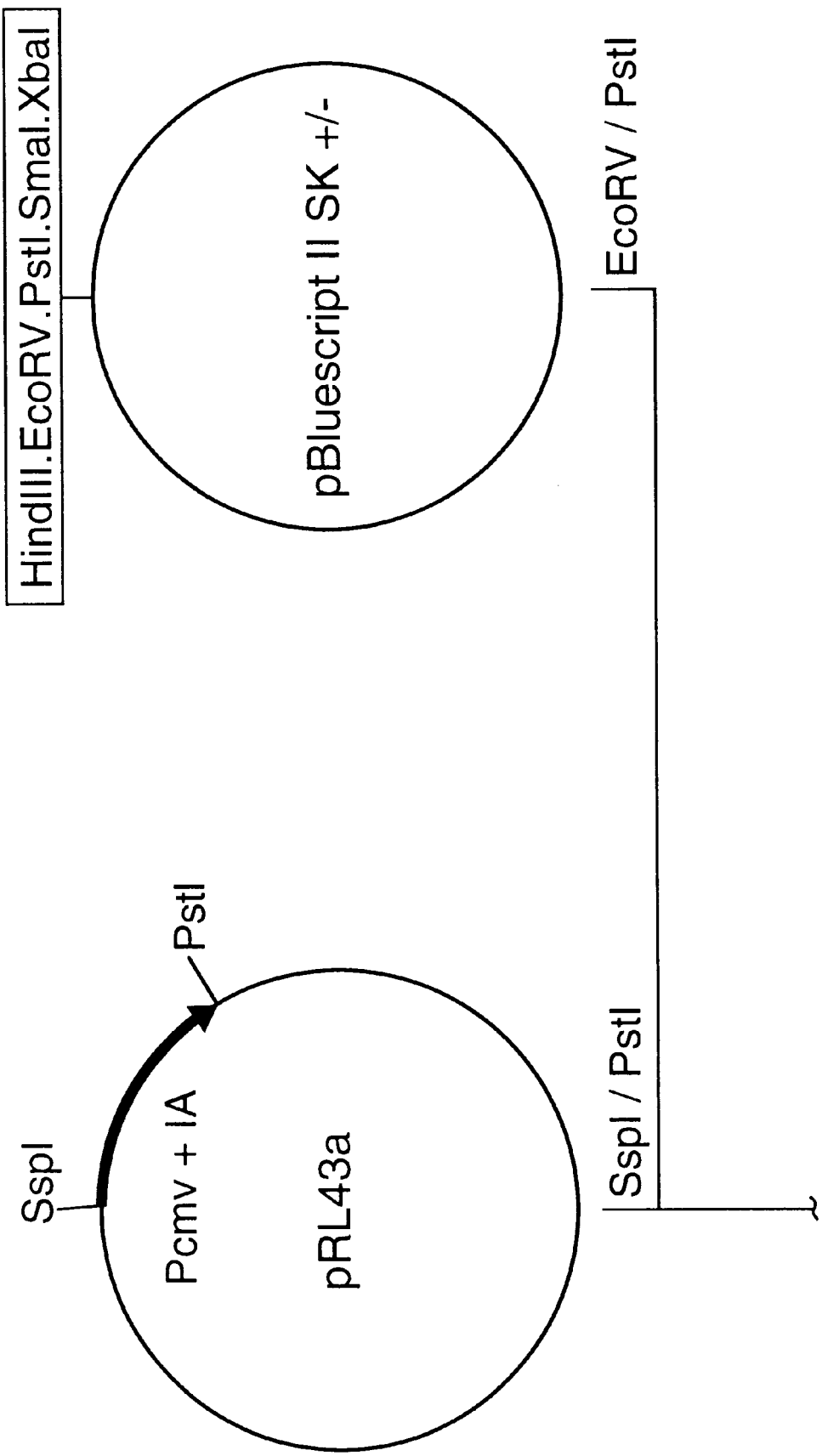
FIGS. 4A, 4B, 4C and 4D show the construction of plasmid pXL1 containing the gene encoding a secreted form of the RSV F protein lacking the transmembrane region.
Figure 4B:
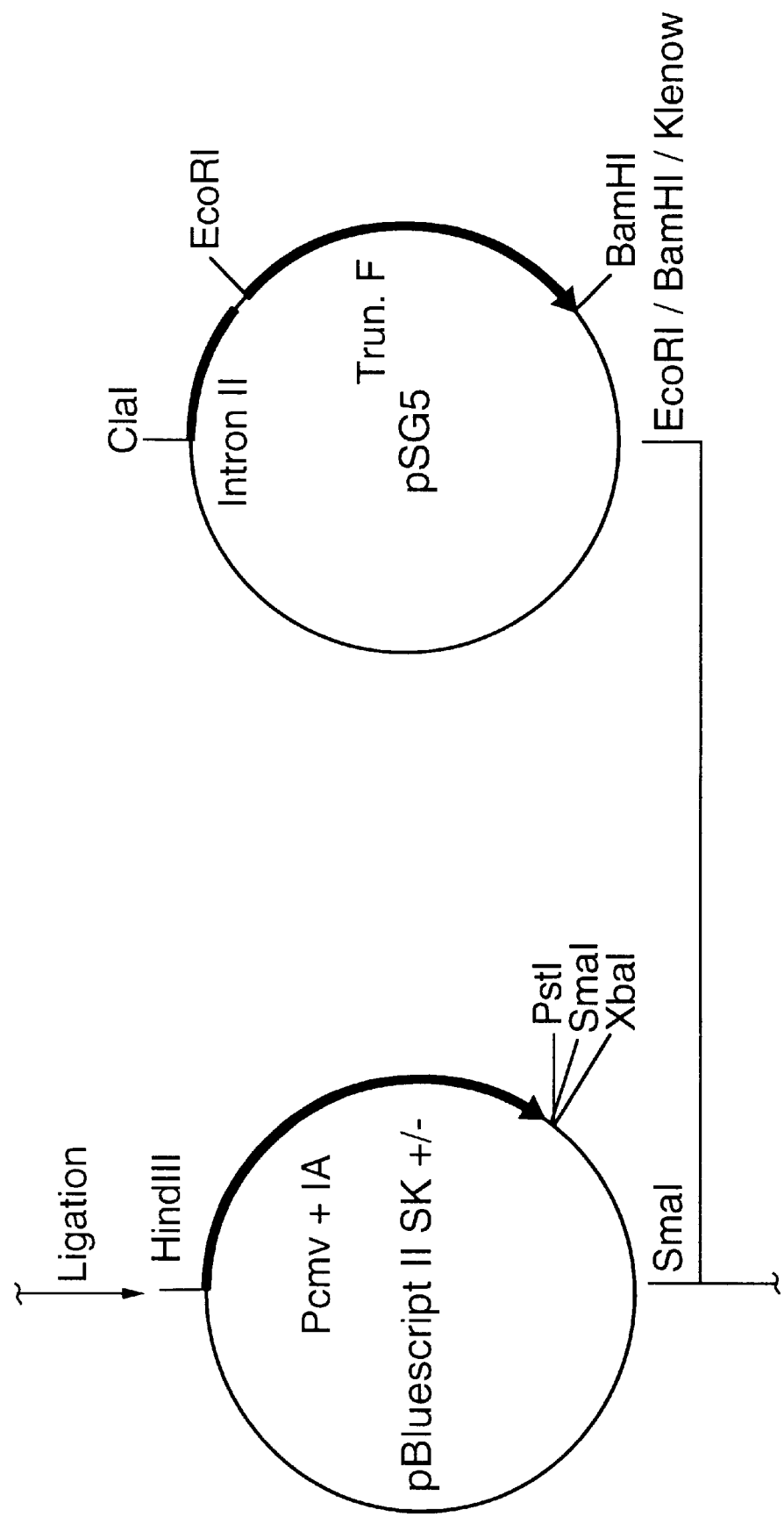
Figure 4C:
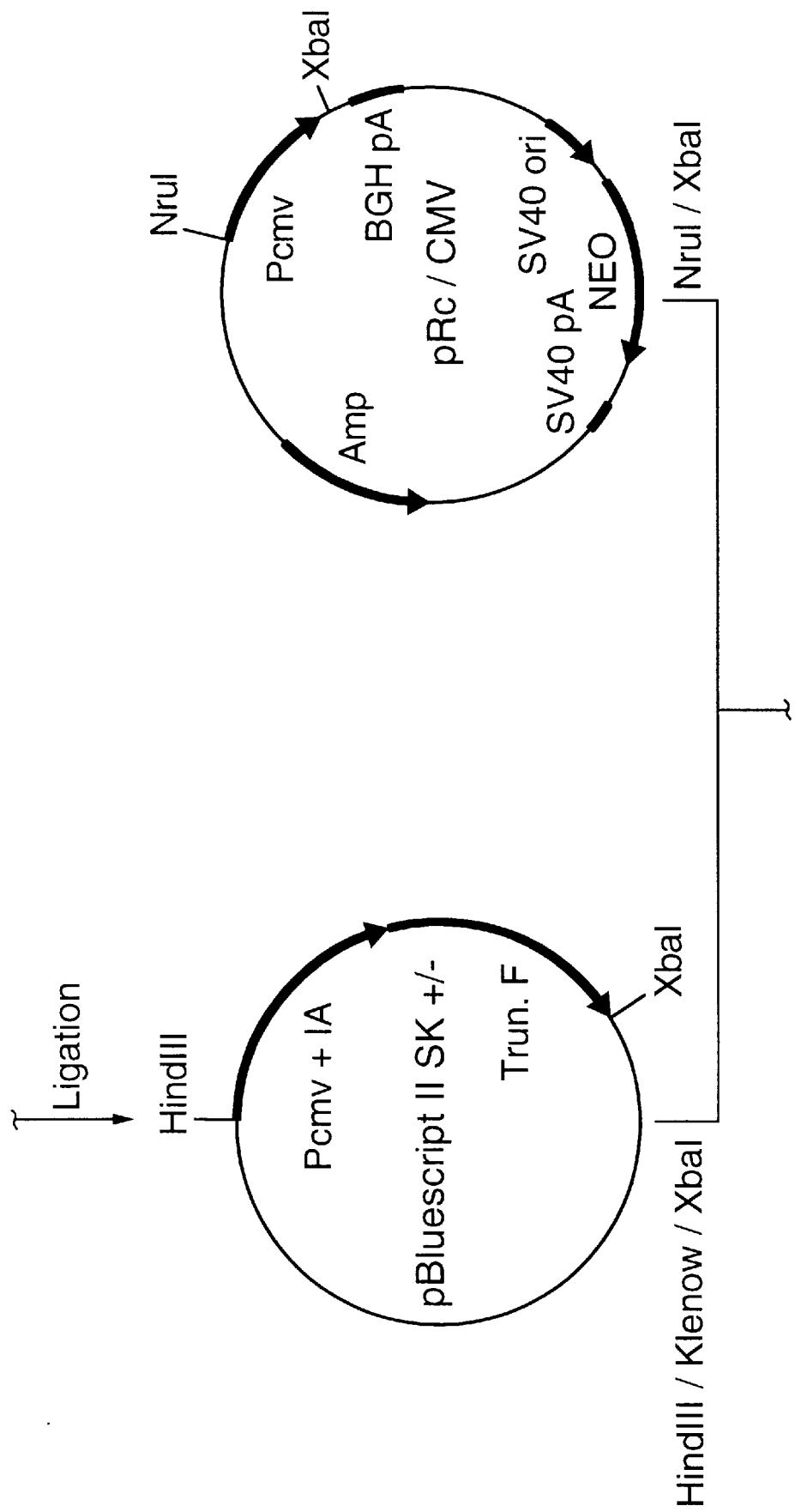
Figure 4D:
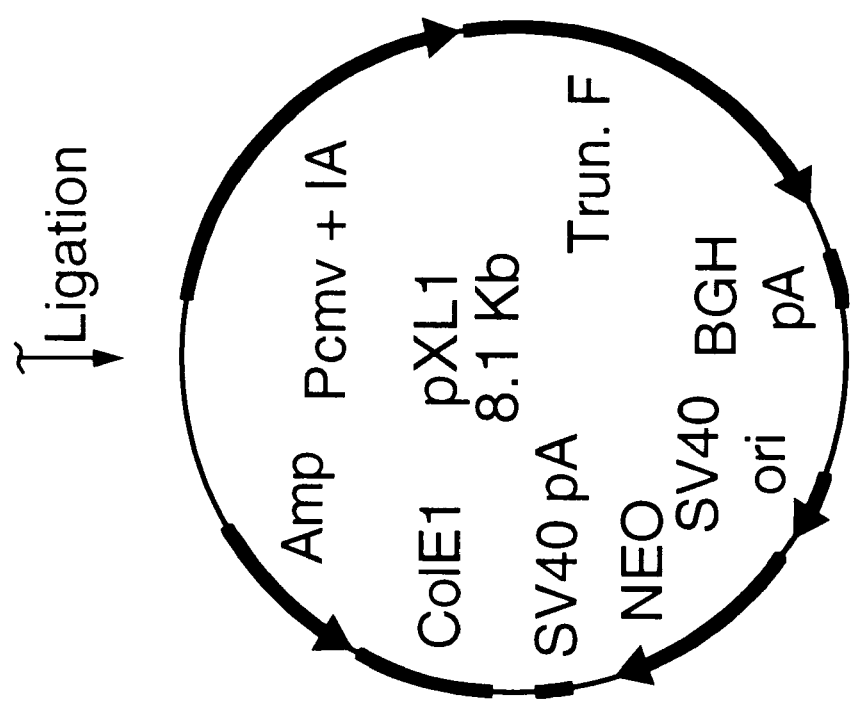
Figure 5A:
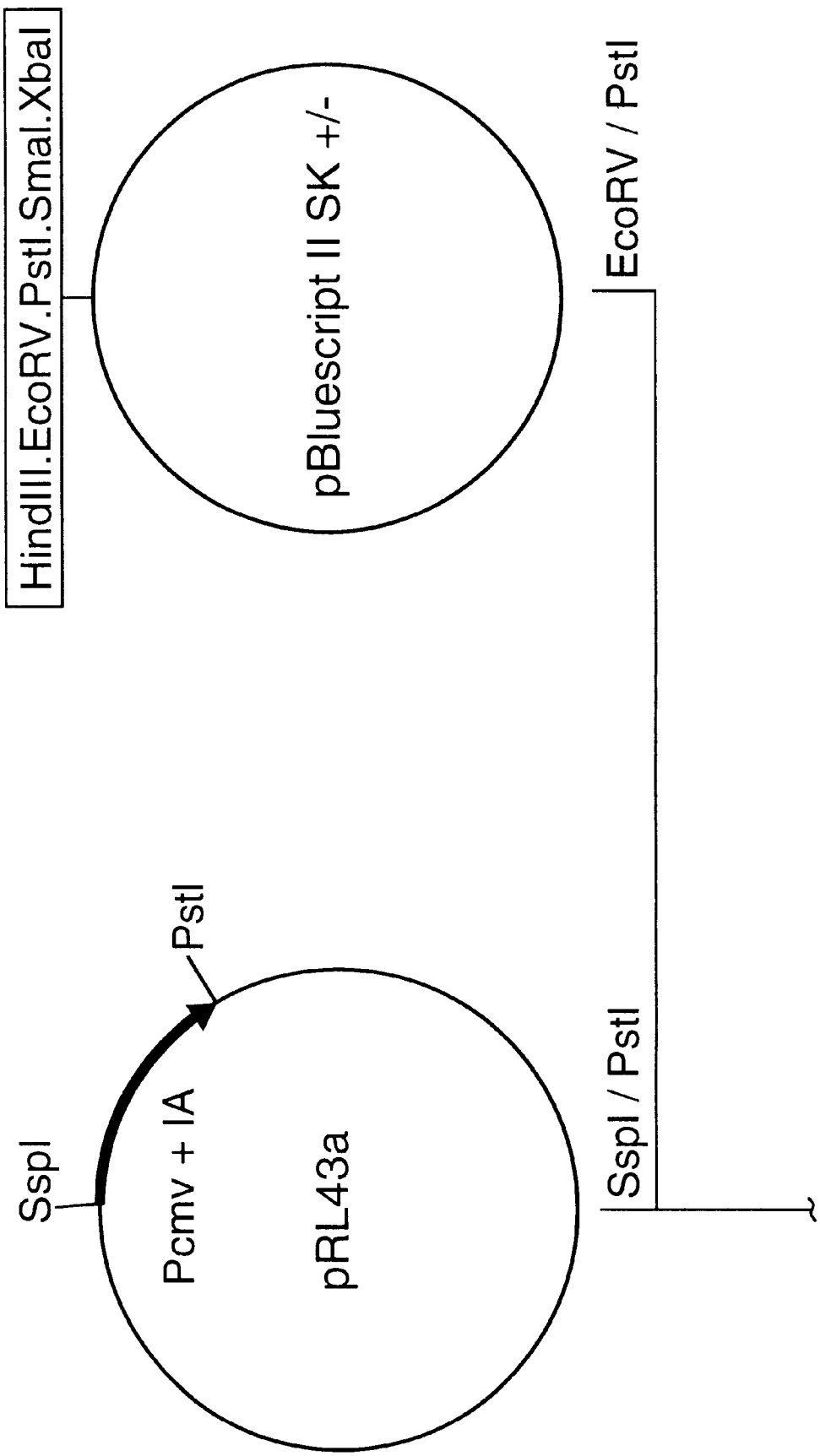
FIGS. 5A, 5B, 5C and 5D show the construction of plasmid pXL2 containing a gene encoding a secreted form of the RSV F protein lacking the transmembrane region and containing the rabbit β-globin Intron II sequence.
Figure 5B:
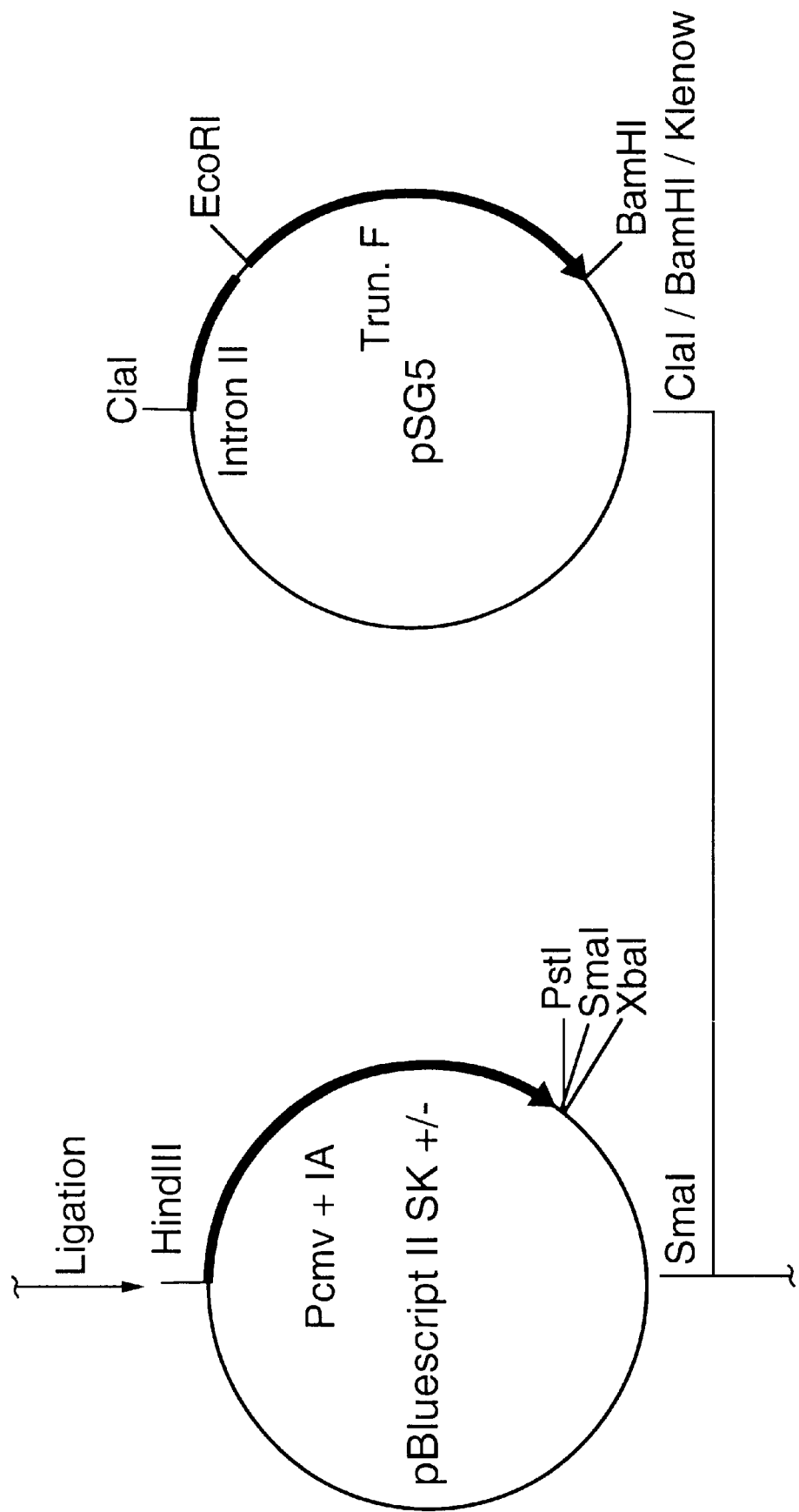
Figure 5C:
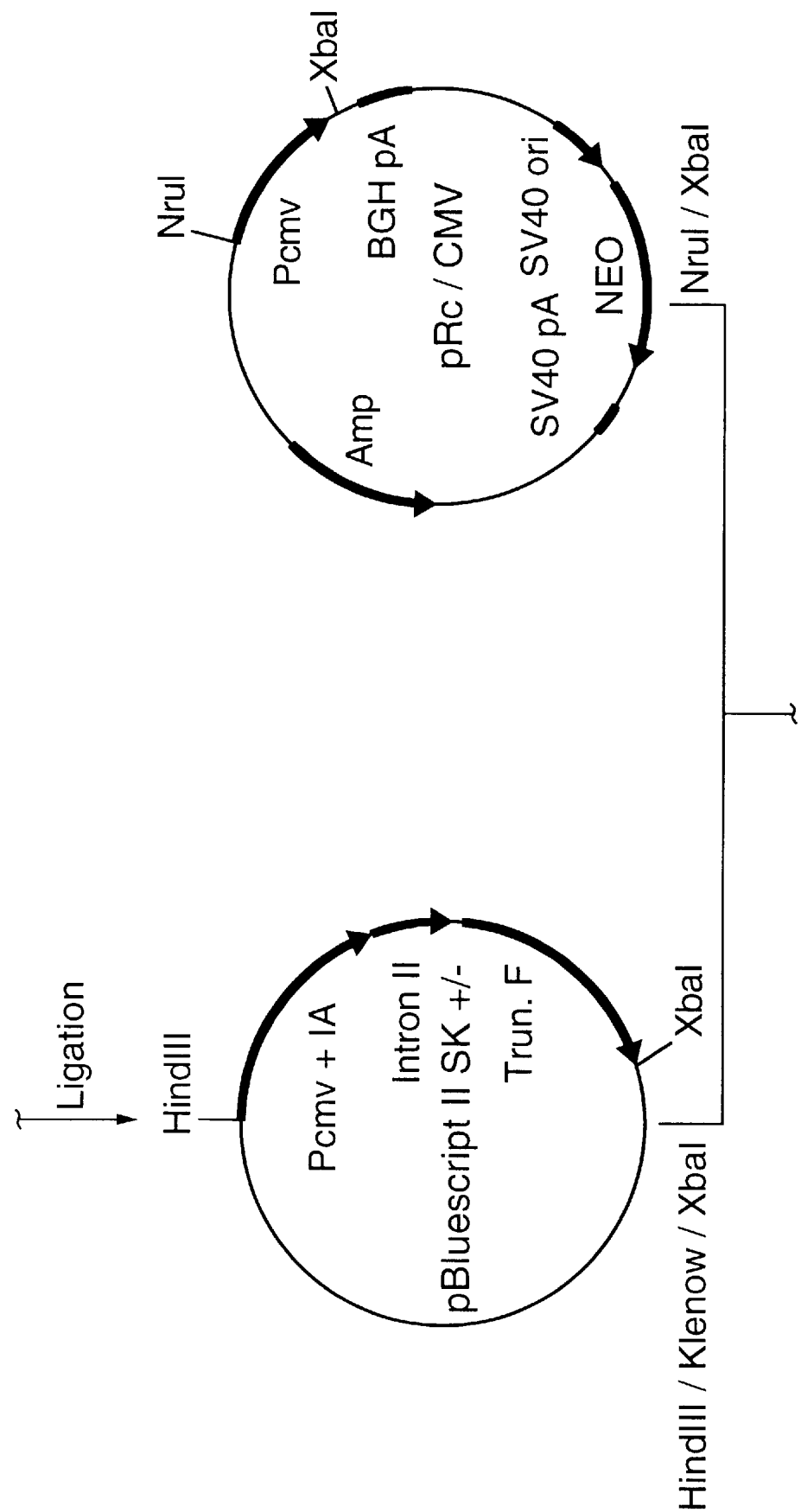
Figure 5D:
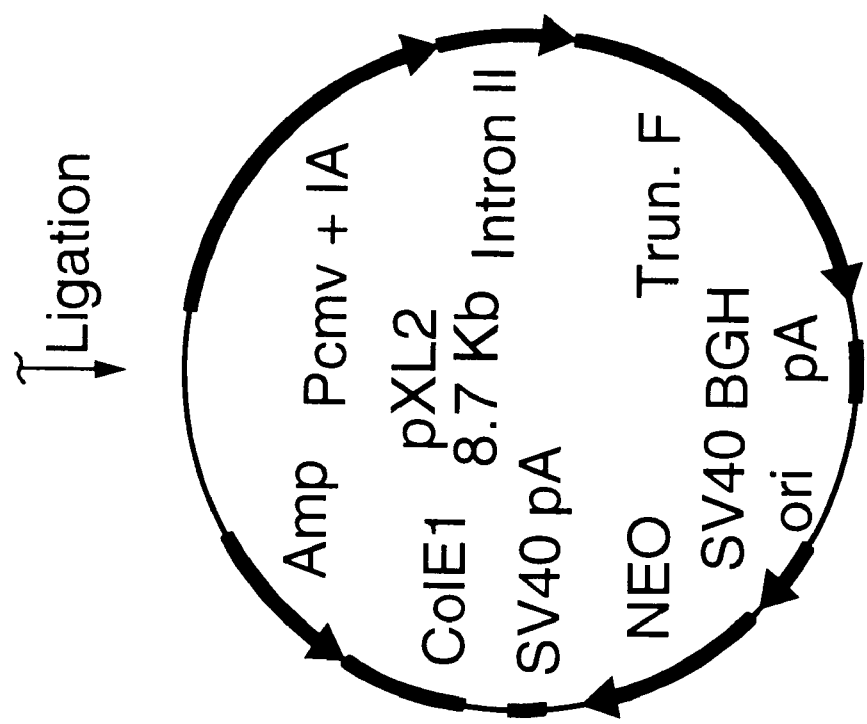
Figure 6A:
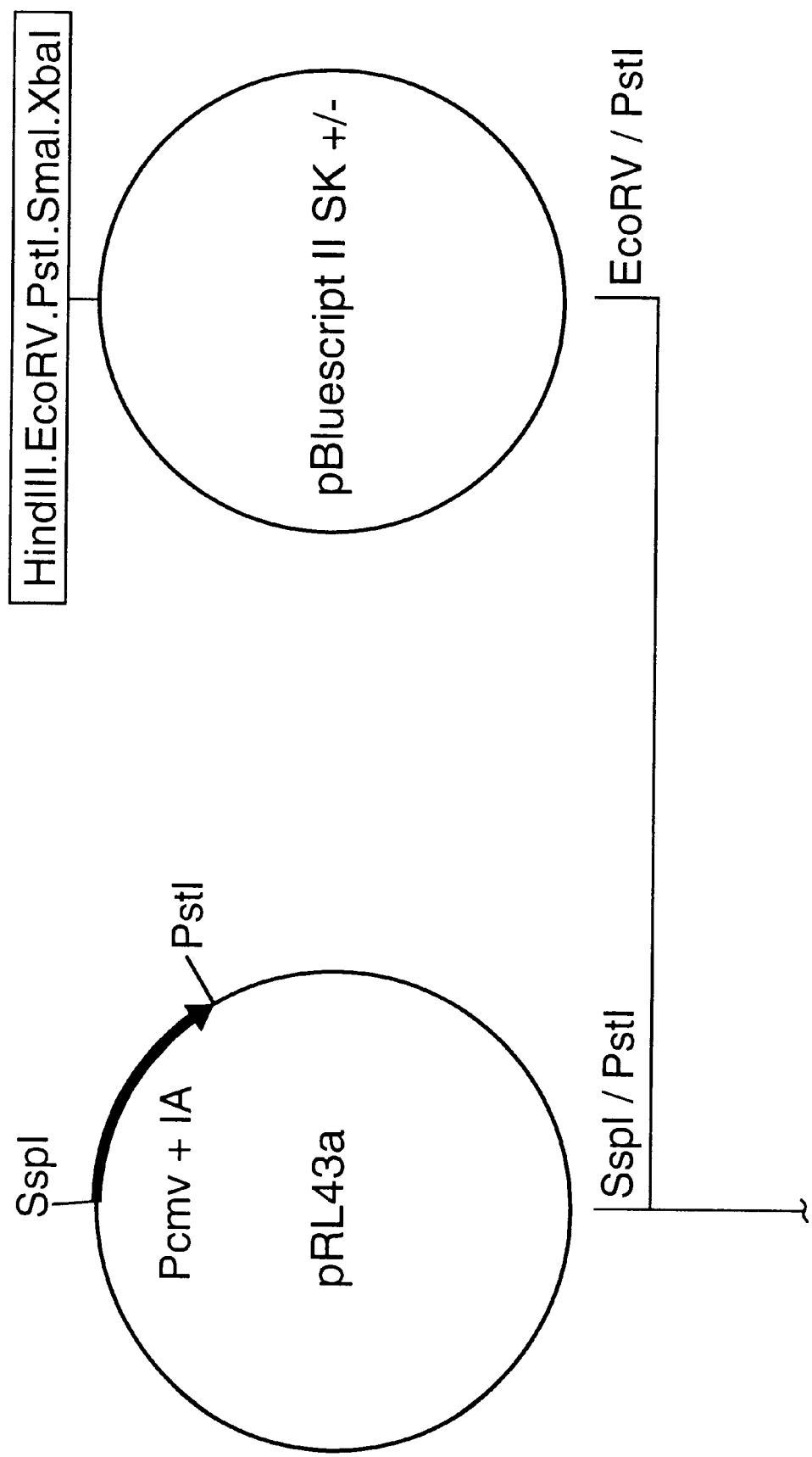
FIGS. 6A, 6B, 6C and 6D show the construction of plasmid pXL3 containing the gene encoding a full length membrane attached form of the RSV F protein.
Figure 6B:
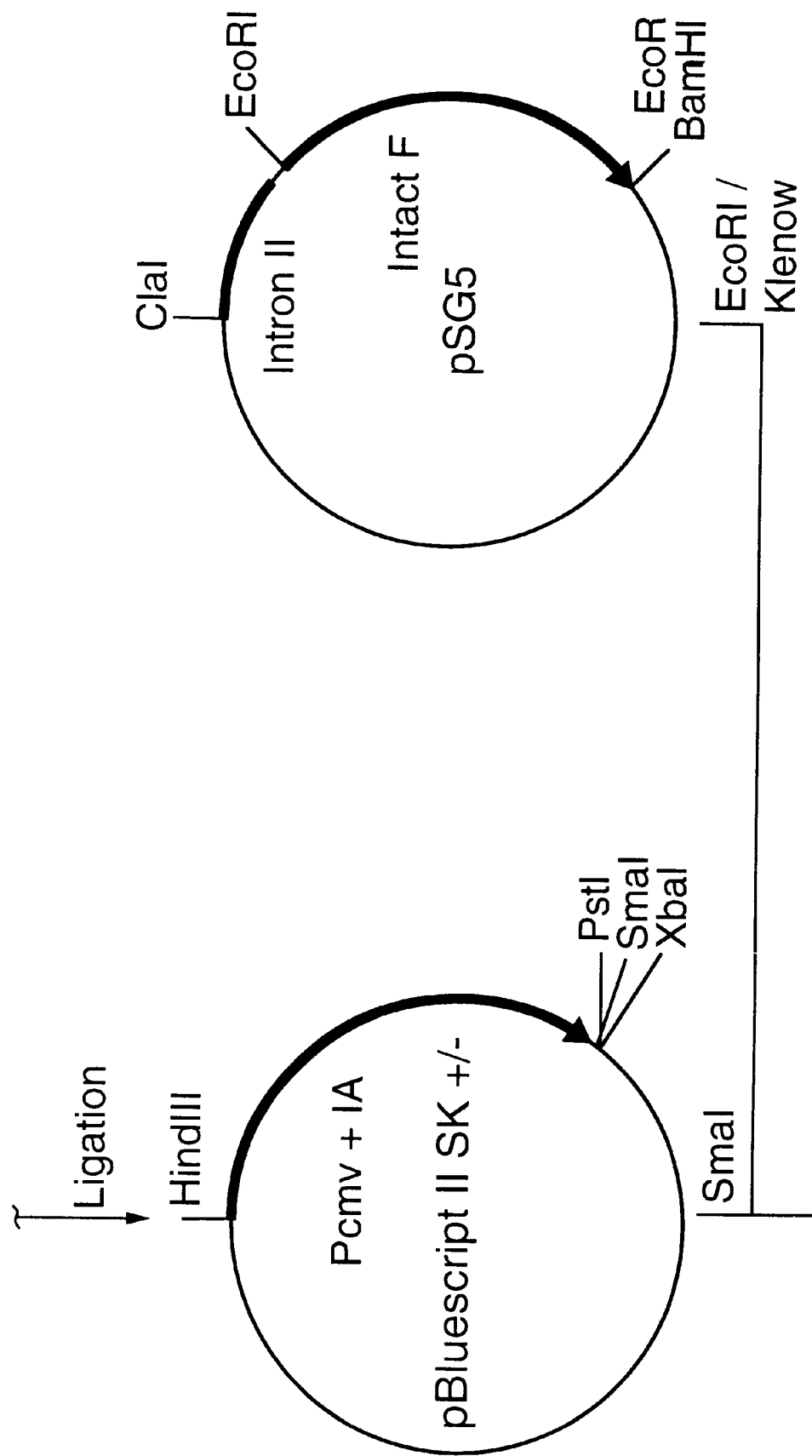
Figure 6C:
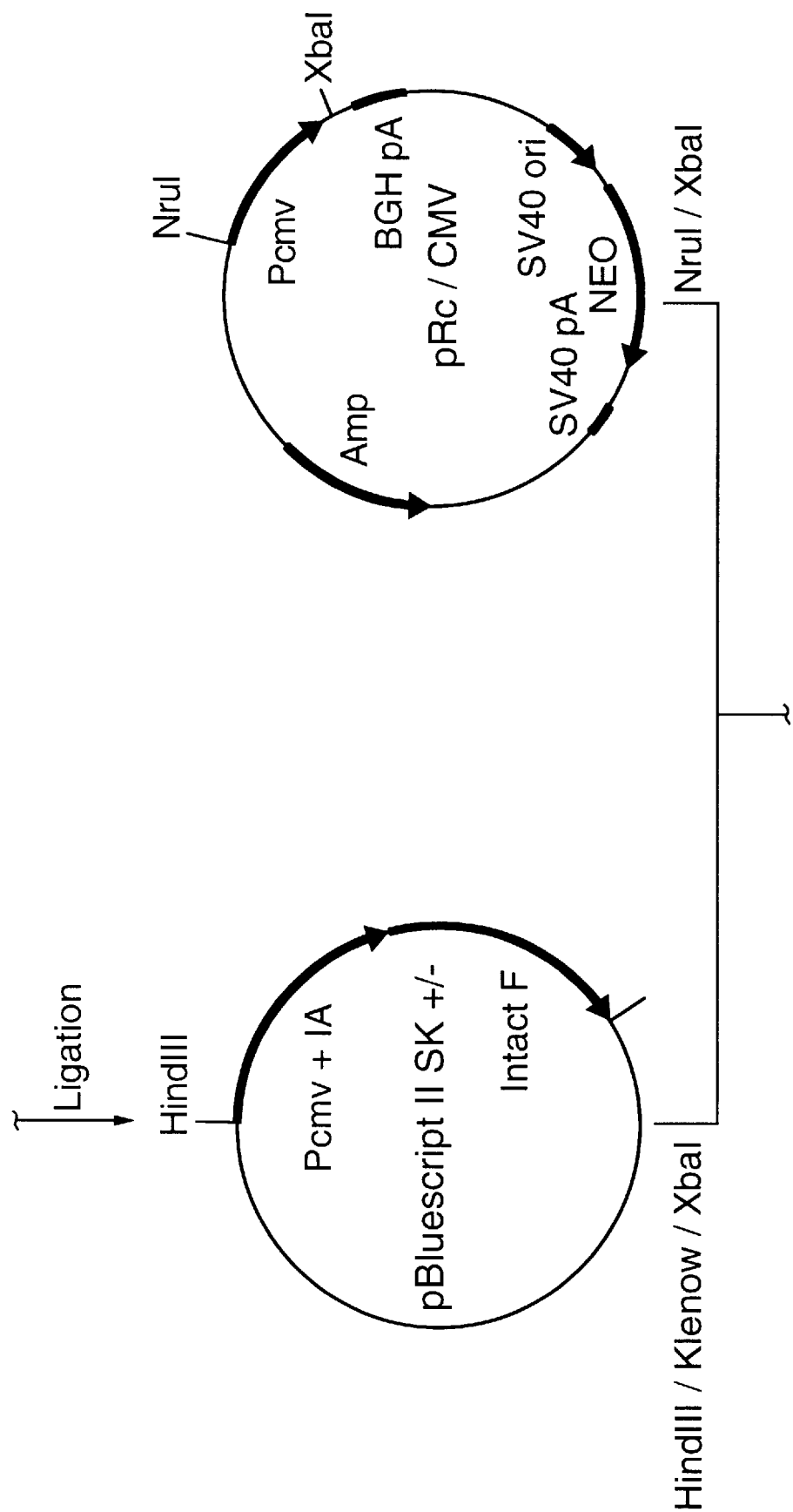
Figure 6D:
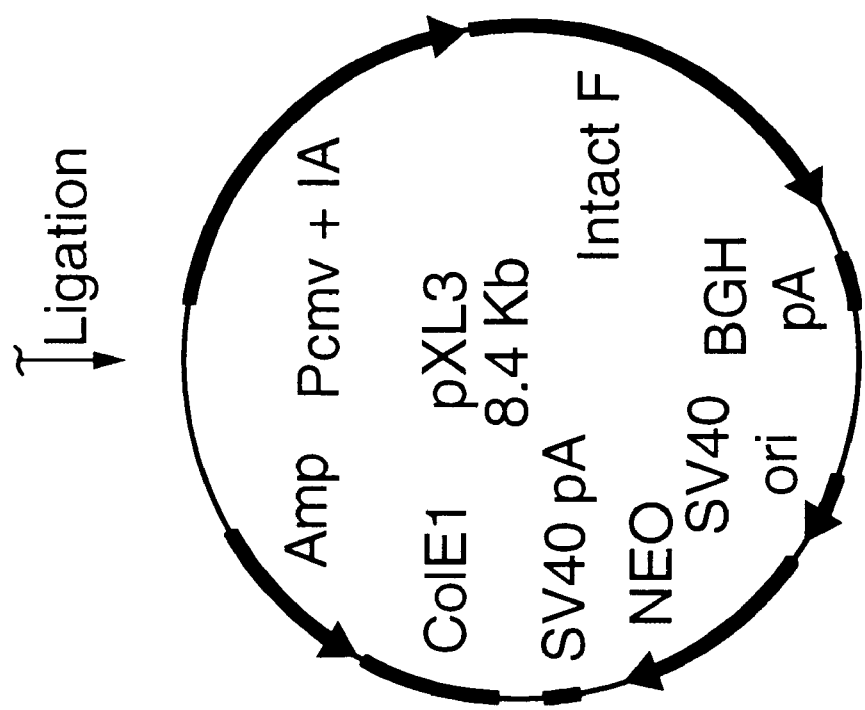
Figure 7A:
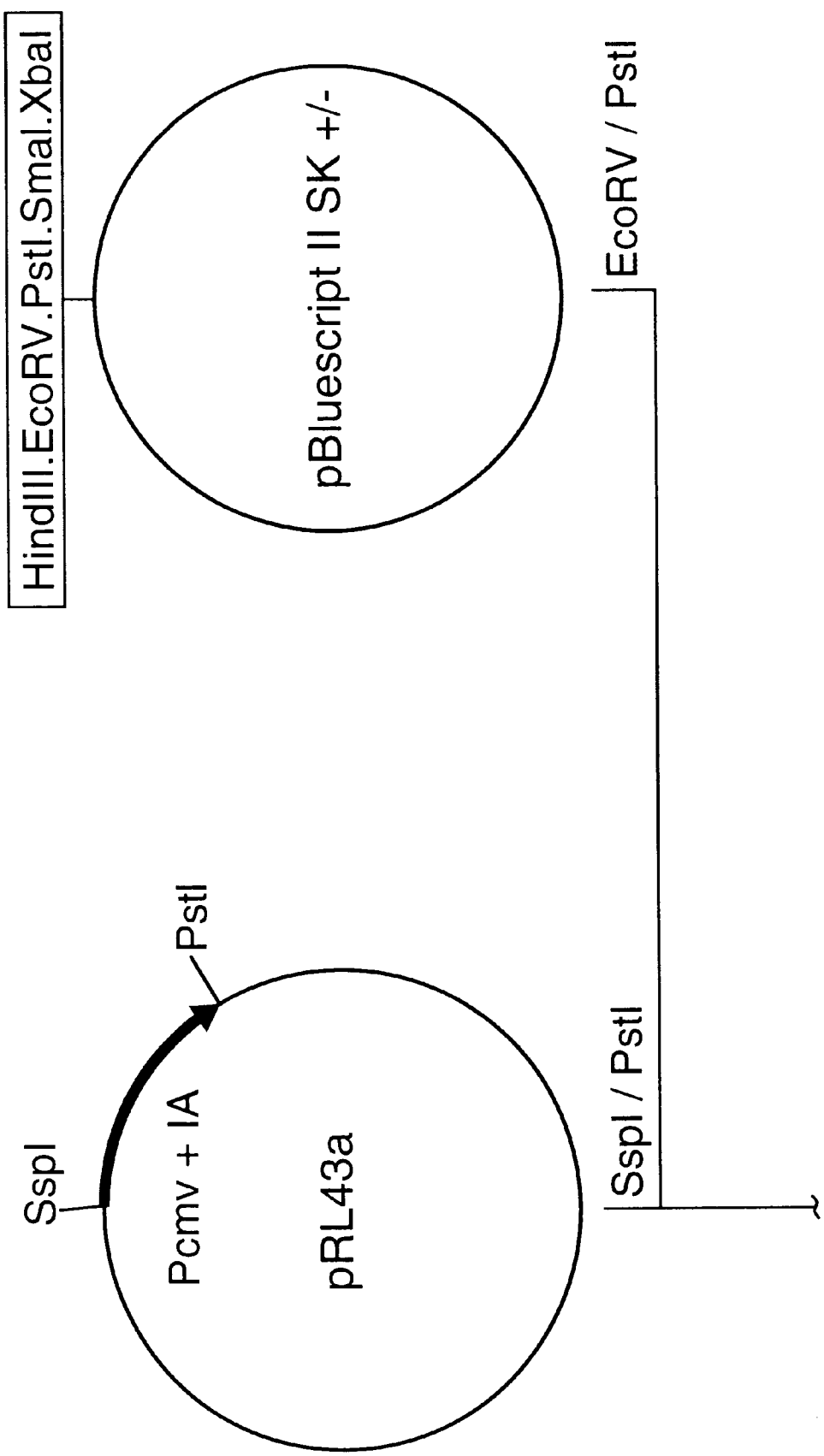
FIGS 7A, 7B, 7C and 7D show the construction of plasmid pXL4 containing a gene encoding a membrane attached form of the RSV F protein and containing the rabbit β-globin Intron II sequence.
Figure 7B:
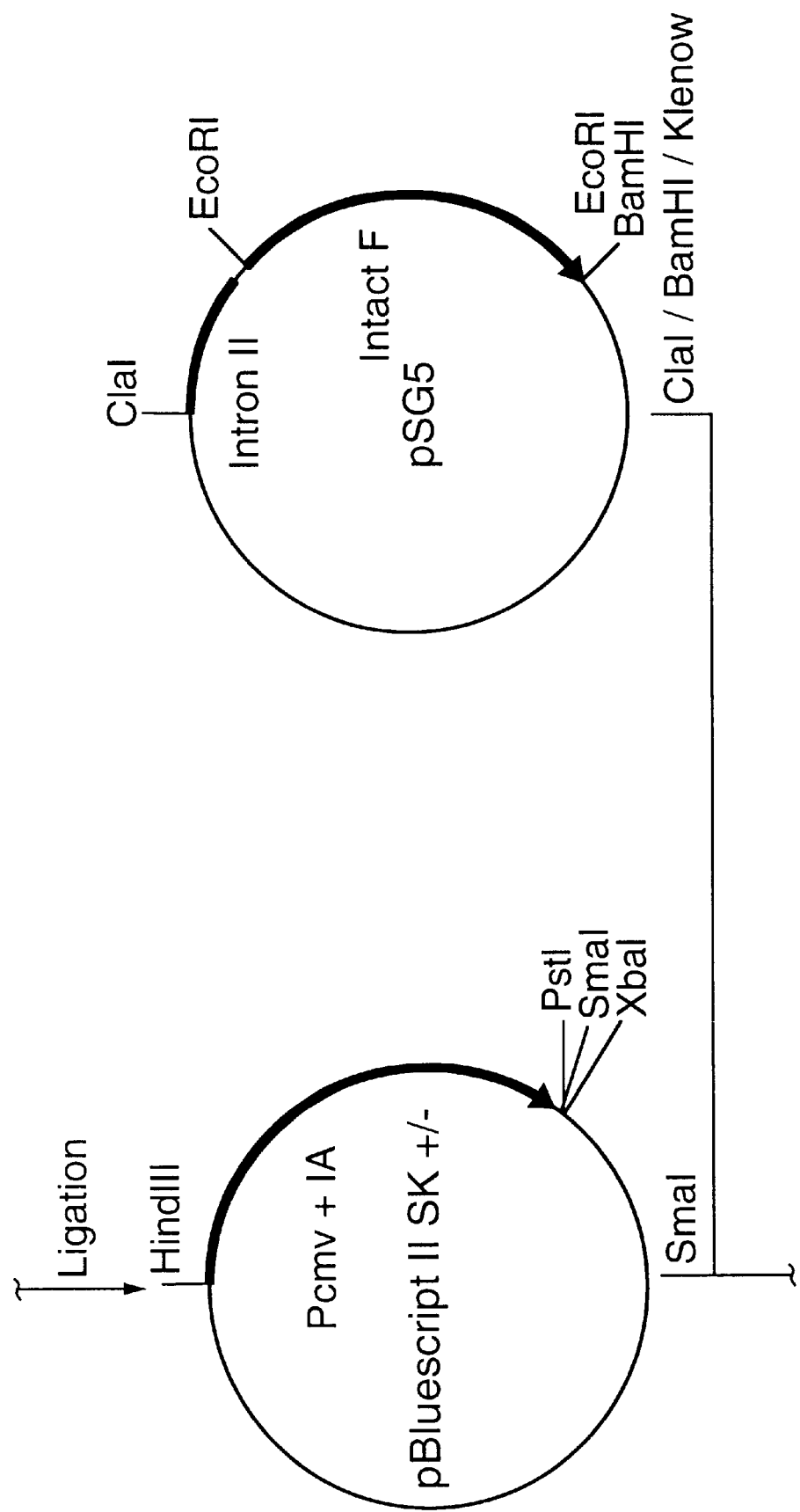
Figure 7C:
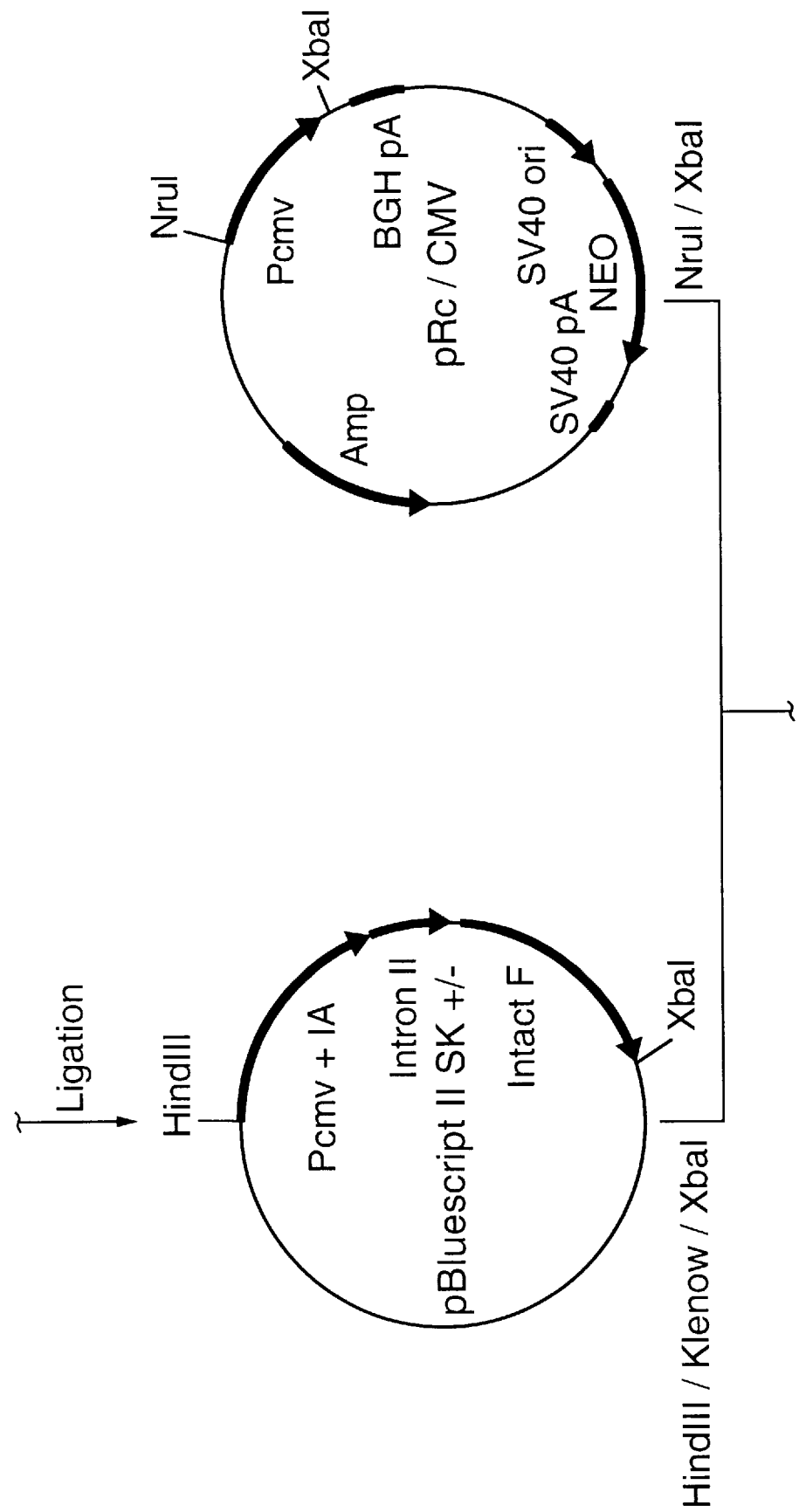
Figure 7D:
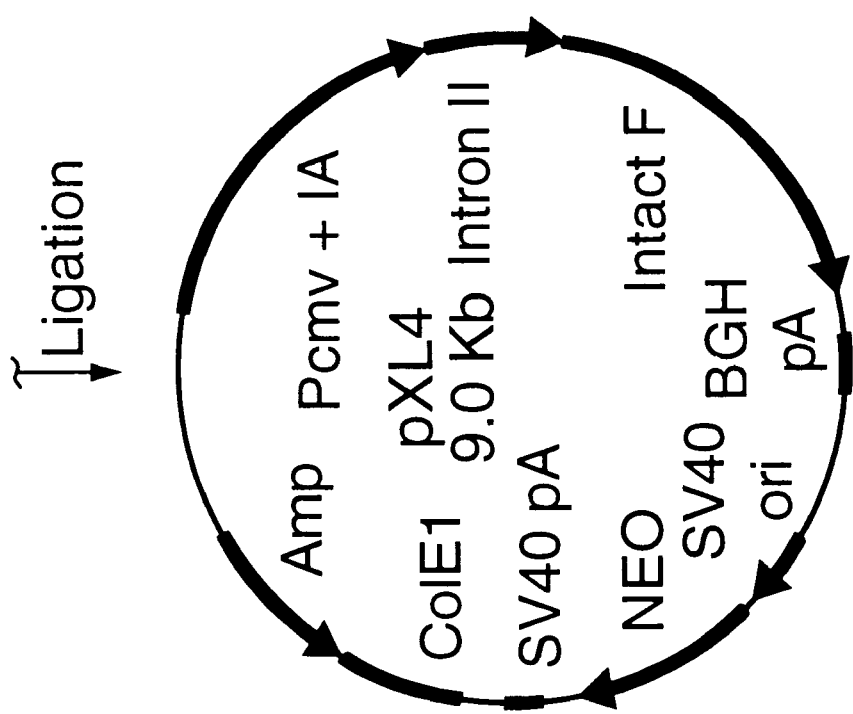

As described above, the present invention relates generally to polynucleotide, including DNA, immunization to obtain protection against infection by respiratory syncytial virus (RSV) and to diagnostic procedures using particular vectors. In the present invention, several recombinant vectors were constructed to contain a nucleotide sequence encoding an RSV F protein.

Figure 2D:
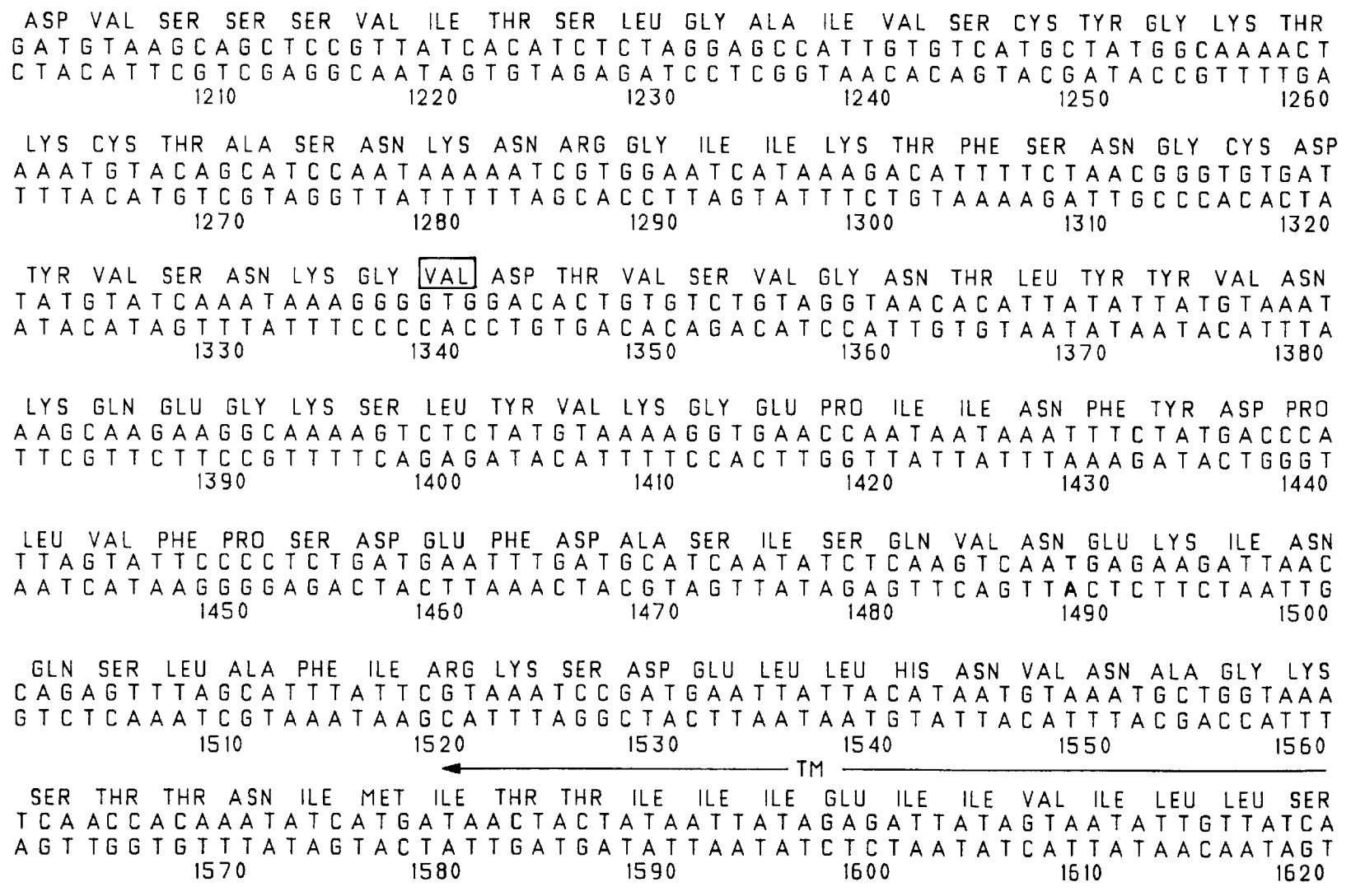

The nucleotide sequence of the full length RSV F gene is shown in FIG. 2 (SEQ ID No: 1). Certain constructs provided herein include the nucleotide sequence encoding the full-length RSV F (SEQ ID No: 2) protein while others include an RSV F gene modified by insertion of termination codons immediately upstream of the transmembrane coding region (see FIG. 3, SEQ ID No: 3), to prevent expression of the transmembrane portion of the protein and to produce a secreted or truncated RSV F protein lacking a transmembrane region (SEQ ID No. 4). In addition, certain constructs provided herein include a nucleic acid sequence encoding a heterologous signal peptide sequence rather than the native signal peptide sequence to provide for enhanced protein expression and increased immunogenicity. Specifically, the signal peptide sequence for HSV I gD is employed. However, other heterologous signal peptides may be employed, such as that of human tissue plasminogen activator (TPA).

The nucleotide sequence encoding the RSV F protein is operatively coupled to a promoter sequence for expression of the encoded RSV F protein. The promoter sequence may be the immediately early cytomegalovirus (CMV) promoter. This promoter is described in ref. 13. Any other convenient promoter may be used, including constitutive promoters, such as, Rous Sarcoma Virus LTRs, and inducible promoters, such as metallothionine promoter, and tissue specific promoters.

The vectors provided herein, when administered to an animal, effect in vivo RSV F protein expression, as demonstrated by an antibody response in the animal to which it is administered. Such antibodies may be used herein in the detection of RSV protein in a sample, as described in more detail below. When the encoded RSV F protein is in the form of an RSV F protein from which the transmembrane region is absent, such as plasmid pXL1 (FIG. 4), the administration of the vector conferred protection in mice and cotton rats to challenge by live RSV virus neutralizing antibody and cell mediated immune responses and an absence of immunopotentiation in immunized animals, as seen from the Examples below.

The recombinant vector also may include a second nucleotide sequence located adjacent the RSV F protein encoding nucleotide sequence to enhance the immunoprotective ability of the RSV F protein when expressed in vivo in a host. Such enhancement may be provided by increased in vivo expression, for example, by increased mRNA stability, enhanced transcription and/or translation. This additional sequence preferably is located between the promoter sequence and the RSV F protein-encoding sequence.

This enhancement sequence may comprise a pair of splice sites to prevent aberrant mRNA splicing during transcription and translation so that substantially all transcribed mRNA encodes an RSV F protein. Specifically, the rabbit β-globin Intron II sequence shown in FIG. 7 (SEQ ID No: 5) may provide such splice sites, as also described in ref. 15.

The construct containing the Intron II sequence, CMV promoter and nucleotide sequence coding for the truncated RSV F protein lacking a transmembrane region, i.e. plasmid pXL2 (FIG. 5), induced complete protection in mice against challenge with live RSV, as seen in the Examples below. In addition, the construct containing the Intron II sequence, CMV promoter and nucleotide sequence coding for the full-length RSV F protein, i.e. plasmid pXL4 (FIG. 7), also conferred protection in mice to challenge with live RSV, as seen from the Examples below. The construct containing the Intron II sequence, CMV promoter, HSV I gD signal peptide peptide encoding sequence and nucleotide sequence coding for the truncated RSV F protein lacking a transmembrane region, i.e. plasmid p82M35B (FIG. 10), induced complete protection in the absence of cardotoxin pretreatment under conditions where pretreatment with cardiotoxin was required for pXL2 to confer complete protection, as seen from the Examples below.

The vector provided herein may also comprise a third nucleotide sequence encoding a further antigen from RSV, an antigen from at least one other pathogen or at least one immunomodulating agent, such as cytokine. Such vector may contain said third nucleotide sequence in a chimeric or a bicistronic structure. Alternatively, vectors containing the third nucleotide sequence may be separately constructed and coadministered to a host, with the nucleic acid molecule provided herein.

It is clearly apparent to one skilled in the art, that the various embodiments of the present invention have many applications in the fields of vaccination, diagnosis and treatment of RSV infections. A further non-limiting discussion of such uses is further presented below.

1. Vaccine Preparation and Use

Immunogenic compositions, suitable to be used as vaccines, may be prepared from the RSV F genes and vectors as disclosed herein. The vaccine elicits an immune response in a subject which includes the production of anti-F antibodies. Immunogenic compositions, including vaccines, containing the nucleic acid may be prepared as injectables, in physiologically-acceptable liquid solutions or emulsions for polynucleotide administration. The nucleic acid may be associated with liposomes, such as lecithin liposomes or other liposomes known in the art, as a nucleic acid liposome (for example, as described in WO 9324640, ref. 17) or the nucleic acid may be associated with an adjuvant, as described in more detail below. Liposomes comprising cationic lipids interact spontaneously and rapidly with polyanions such as DNA and RNA, resulting in liposome/nucleic acid complexes that capture up to 100% of the polynucleotide. In addition, the polycationic complexes fuse with cell membranes, resulting in an intracellular delivery of polynucleotide that bypasses the degradative enzymes of the lysosomal compartment. Published PCT application WO 94/27435 describes compositions for genetic immunization comprising cationic lipids and polynucleotides. Agents which assist in the cellular uptake of nucleic acid, such as calcium ions, viral proteins and other transfection facilitating agents, may advantageously be used.

Polynucleotide immunogenic preparations may also be formulated as microcapsules, including biodegradable time-release particles. Thus, U.S. Pat. No. 5,151,264 describes a particulate carrier of a phospholipid/glycolipid/polysaccharide nature that has been termed Bio Vecteurs Supra Moleculaires (BVSM). The particulate carriers are intended to transport a variety of molecules having biological activity in one of the layers thereof.

U.S. Pat. No. 5,075,109 describes encapsulation of the antigens trinitrophenylated keyhole limpet hemocyanin and staphylococcal enterotoxin B in 50:50 poly (DL-lactideco-glycolide). Other polymers for encapsulation are suggested, such as poly(glycolide), poly(DL-lactide-co-glycolide), copolyoxalates, polycaprolactone, poly(lactide-co-caprolactone), poly(esteramides), polyorthoesters and poly (8-hydroxybutyric acid), and polyanhydrides.

Published PCT application WO 91/06282 describes a delivery vehicle comprising a plurality of bioadhesive microspheres and antigens. The microspheres being of starch, gelatin, dextran, collagen or albumin. This delivery vehicle is particularly intended for the uptake of vaccine across the nasal mucosa. The delivery vehicle may additionally contain an absorption enhancer.

The RSV F genes and vectors may be mixed with pharmaceutically acceptable excipients which are compatible therewith. Such excipients may include, water, saline, dextrose, glycerol, ethanol, and combinations thereof. The immunogenic compositions and vaccines may further contain auxiliary substances, such as wetting or emulsifying agents, pH buffering agents, or adjuvants to enhance the effectiveness thereof. Immunogenic compositions and vaccines may be administered parenterally, by injection subcutaneously, intravenously, intradermally or intramuscularly, possibly following pretreatment of the injection site with a local anesthetic. Alternatively, the immunogenic compositions formed according to the present invention, may be formulated and delivered in a manner to evoke an immune response at mucosal surfaces. Thus, the immunogenic composition may be administered to mucosal surfaces by, for example, the nasal or oral (intragastric) routes. Alternatively, other modes of administration including suppositories and oral formulations may be desirable. For suppositories, binders and carriers may include, for example, polyalkalene glycols or triglycerides. Oral formulations may include normally employed incipients, such as, for example, pharmaceutical grades of saccharine, cellulose and magnesium carbonate.

The immunogenic preparations and vaccines are administered in a manner compatible with the dosage formulation, and in such amount as will be therapeutically effective, protective and immunogenic. The quantity to be administered depends on the subject to be treated, including, for example, the capacity of the individual's immune system to synthesize the PSV F protein and antibodies thereto, and if needed, to produce a cell-mediated immune response. Precise amounts of active ingredient required to be administered depend on the judgment of the practitioner. However, suitable dosage ranges are readily determinable by one skilled in the art and may be of the order of about 1 µg to about 11 mg of the RSV F genes and vectors. Suitable regimes for initial administration and booster doses are also variable, but may include an initial administration followed by subsequent administrations. The dosage may also depend on the route of administration and will vary according to the size of the host. A vaccine which protects against only one pathogen is a monovalent vaccine. Vaccines which contain antigenic material of several pathogens are combined vaccines and also belong to the present invention. Such combined vaccines contain, for example, material from various pathogens or from various strains of the same pathogen, or from combinations of various pathogens.

Immunogenicity can be significantly improved if the vectors are co-administered with adjuvants, commonly used as 0.05 to 0.1 percent solution in phosphate-buffered saline. Adjuvants enhance the immunogenicity of an antigen but are not necessarily immunogenic themselves. Adjuvants may act by retaining the antigen locally near the site of administration to produce a depot effect facilitating a slow, sustained release of antigen to cells of the immune system. Adjuvants can also attract cells of the immune system to an antigen depot and stimulate such cells to elicit immune responses.

Immunostimulatory agents or adjuvants have been used for many years to improve the host immune responses to, for example, vaccines. Thus, adjuvants have been identified that enhance the immune response to antigens. Some of these adjuvants are toxic, however, and can cause undesirable side-effects, making them unsuitable for use in humans and many animals. Indeed, only aluminum hydroxide and aluminum phosphate (collectively commonly referred to as alum) are routinely used as adjuvants in human and veterinary vaccines.

A wide range of extrinsic adjuvants and other immunomodulating material can provoke potent immune responses to antigens. These include saponins complexed to membrane protein antigens to produce immune stimulating complexes (ISCOMS), pluronic polymers with mineral oil, killed mycobacteria in mineral oil, Freund's complete adjuvant, bacterial products, such as muramyl dipeptide (MDP) and lipopolysaccharide (LPS), as well as monophoryl lipid A, QS 21 and polyphosphazene.

In particular embodiments of the present invention, the vector comprising a first nucleotide sequence encoding an F protein of RSV may be delivered in conjunction with a targeting molecule to target the vector to selected cells including cells of the immune system.

The polynucleotide may be delivered to the host by a variety of procedures, for example, Tang et al. (ref. 10) disclosed that introduction of gold microprojectiles coated with DNA encoding bovine growth hormone (BGH) into the skin of mice resulted in production of anti-BGH antibodies in the mice, while Furth et al. (ref. 11) showed that a jet injector could be used to transfect skin, muscle, fat and mammary tissues of living animals.

2. Immunoassays

The RSV F genes and vectors of the present invention are useful as immunogens for the generation of anti-F antibodies for use in immunoassays, including enzyme-linked immunosorbent assays (ELISA), RIAs and other non-enzyme linked antibody binding assays or procedures known in the art. In ELISA assays, the vector first is administered to a host to generate antibodies specific to the RSV F protein. These RSV F-specific antibodies are immobilized onto a selected surface, for example, a surface capable of binding the antibodies, such as the wells of a polystyrene microtiter plate. After washing to remove incompletely adsorbed antibodies, a nonspecific protein such as a solution of bovine serum albumin (BSA) that is known to be antigenically neutral with regard to the test sample may be bound to the selected surface. This allows for blocking of nonspecific adsorption sites on the immobilizing surface and thus reduces the background caused by nonspecific bindings of antisera onto the surface.

The immobilizing surface is then contacted with a sample, such as clinical or biological materials, to be tested in a manner conducive to immune complex (antigen/antibody) formation. This procedure may include diluting the sample with diluents, such as solutions of BSA, bovine gamma globulin (BGG) and/or phosphate buffered saline (PBS)/Tween. The sample is then allowed to incubate for from about 12 to 4 hours, at temperatures such as of the order of about 120° to 37° C. Following incubation, the sample-contacted surface is washed to remove non-immunocomplexed material. The washing procedure may include washing with a solution, such as PBS/Tween or a borate buffer. Following formation of specific immunocomplexes between the test sample and the bound RSV F specific antibodies, and subsequent washing, the occurrence, and even amount, of immunocomplex formation may be determined.

BIOLOGICAL MATERIALS

Certain plasmids that contain the gene encoding RSV F protein and referred to herein have been deposited with the America Type Culture Collection (ATCC) located at 10801 University Blvd., Manassas, Va. 20110-2209, U.S.A., pursuant to the Budapest Treaty and prior to the filing of this application.

Samples of the deposited plasmids will become available to the public upon grant of a patent based upon this United States patent application and all restrictions on access to the deposits will be removed at that time. The deposits will be replaced if the Depository is unable to dispense viable samples. The invention described and claimed herein is not to be limited in scope by plasmids deposited, since the deposited embodiment is intended only as an illustration of the invention. Any equivalent or similar plasmids that encode similar or equivalent antigens as described in this application are within the scope of the invention.

| Plasmid | ATCC Designation | Date Deposited |
|---|---|---|
| pXL1 | 97167 | May 30, 1995 |
| pXL2 | 97168 | May 30, 1995 |
| pXL3 | 97169 | May 30, 1995 |
| pXL4 | 97170 | May 30, 1995 |
| p82M35B | 203790 | February 23, 1999 |

EXAMPLES

The above disclosure generally describes the present invention. A more complete understanding can be obtained by reference to the following specific Examples. These Examples are described solely for purposes of illustration and are not intended to limit the scope of the invention. Changes in form and substitution of equivalents are contemplated as circumstances may suggest or render expedient. Although specific terms have been employed herein, such terms are intended in a descriptive sense and not for purposes of limitations.

Methods of molecular genetics, protein biochemistry, and immunology used but not explicitly described in this disclosure and these Examples are amply reported in the scientific literature and are well within the ability of those skilled in the art.

Example 1

This Example describes the construction of vectors containing the RSV F gene.

FIG. 1 shows a restriction map of the gene encoding the F protein of Respiratory Syncytial Virus and FIG. 2 shows the nucleotide sequence of the gene encoding the full-length RSV F protein (SEQ ID No: 1) and the deduced amino acid sequence (SEQ ID No: 2). FIG. 3 shows the gene encoding the secreted RSV F protein (SEQ ID No: 3) and the deduced amino acid sequence (SEQ ID No: 4).

A set of four plasmid DNA constructs were made (as shown schematically in FIGS. 4 to 7) in which cDNA encoding the RSV-F was subcloned downstream of the immediate-early promoter, enhancer and intron A sequences of human cytomegalovirus (CMV) and upstream of the bovine growth hormone (BGH) poly-A site. The 1.6 Kb Sspl-PstI fragment containing the promoter, enhancer and intron A sequences of CMV Towne strain were initially derived from plasmid pRL43a obtained from Dr. G. S. Hayward of Johns Hopkins University (ref. 20) and subcloned between EcoRV and PstI sites of pBluescript 11 SK +/− (Stratagene). For the construction of plasmids expressing the secretory form of the F protein (pXL1 and pXL2 in FIGS. 4 and 5), the 1.6 Kb EcoRI-BamHI fragment containing the truncated form of the F cDNA originally cloned from a clinical isolate belonging to subgroup A was excised from pRSVF (ref. 18 and WO 93/14207) and subcloned between EcoRI and BamHI sites of pSG5 (Strategene, ref. 14). Either the 1.6 kb EcoRI-BamHI fragment or the 2.2 kb ClaI-BamHI fragment was then excised from the pSG5 construct, filled-in with Klenow and subcloned at the SmaI site of the pBluescript II SK +/− construct containing the promoter and intron A sequences. The 0.6 kb ClaI-EcoPI fragment derived from pSG5 contained the intron II sequences from rabbit β-globin. Subsequently, the plasmids were digested with HindIII, filled-in with Klenow, and digested with XbaI to yield either a 3.2 or a 3.8 Kb fragment. These fragments were used to replace the 0.8 kb NruI-XbaI fragment containing the CMV promoter in pRc/CMV (Invitrogen), resulting in the final pXL1 and pXL2 constructs, respectively.

For the construction of plasmids expressing the full-length F protein (pXL3 and pXL4—FIGS. 6 and 7), the full length RSV F cDNA was excised as a 1.9 kb EcoRI fragment from a recombinant pBluescript M13-SK (Stratagene) containing the insert (ref. 18 and WO 93/14207) and subcloned at the EcoRI site of pSG5 (Stratagene). Either the 1.9 Kb EcoRI fragment or the 2.5 Kb ClaI-BamHI fragment was then excised from the pSG5 construct, filled-in with Klenow and subcloned at the SmaI site of the pBluescript II SK +/− construct containing the promoter and intron A sequences. The rest of the construction for pXL3 and pXL4 was identical to that for pXL1 and pXL2, as described above. Therefore, except for the CMV promoter and intron A sequences, the rest of the vector components in pXL1–4 were derived from plasmid pRc/CMV. Plasmids pXL1 and pXL2 were made to express a truncated/secretory form of the F protein which carried stop codons resulting in a C-terminal deletion of 48 amino acids including the trans-membrane (TM) and the C-terminal cytosolic tail as compared to the intact molecule. In contrast, pXL3 and pXL4 were made to express the intact membrane-attached form of the RSV F molecule containing the TM and the cytosolic C-terminal tail. The rationale for the presence of the intron II sequences in pXL2 and pXL4 was that this intron was reported to mediate the correct splicing of RNAs. Since mRNA for the RSV-F has been suspected to have a tendency towards aberrant splicing, the presence of the intron II sequences might help to overcome this. All four plasmid constructs were confirmed by DNA sequencing analysis.

Plasmid DNA was purified using plasmid mega kits from Qiagen (Chatsworth, Calif., USA) according to the manufacturer's instructions.

Example 2

This Example describes the immunization of mice. Mice are susceptible to infection by RSV as described in ref. 16.

For intramuscular (i.m) immunization, the anterior tibialis anterior muscles of groups of 9 BALB/c mice (male, 6–8 week old) (Jackson Lab., Bar Harbor, Me., USA) were bilaterally injected with 2×50 µg (1 µg/µL in PBS) of pXL1-4, respectively. Five days prior to DNA injection, the muscles were treated with 2×50 µL (10 µM in PBS) of cardiotoxin (Latoxan, France). Pretreatment of the muscles with cardiotoxin has been reported to increase DNA uptake and to enhance the subsequent immune responses by the intramuscular route (ref. 24). These animals were similarly boosted a month later. Mice in the control group were immunized with a placebo plasmid containing identical vector backbone sequences without the RSV F gene according to the same schedule. For intradermal (i.d.) immunization, 100 µg of pXL2 (2 µg/µL in PBS) were injected into the skin 1–2 cm distal from the tall base. The animals were similarly boosted a month later.

Seventy-five days after the second immunization, mice were challenged intranasally with $10^{5.4}$ plaque forming units (pfu) of mouse-adapted RSV, A2 subtype (obtained from Dr. P. Wyde, Baylor College of Medicine, Houston, Tex., USA). Lungs were aseptically removed 4 days later, weighed and homogenized in 2 mL of complete culture medium. The number of pfu in lung homogenates was determined in duplicates as previously described (ref. 19) using vaccine quality Vero cells. These data were subjected to statistic analysis using SigmaStat (Jandel Scientific Software, Guelph, Ont. Canada).

Sera obtained from immunized mice were analyzed for anti-RSV F antibody titres (IgG, IgG1 and IgG2a, respectively) by enzyme-linked immunosorbent assay (ELISA) and for RSV-specific plaque-reduction titres. ELISA were performed using 96-well plates coated with immunoaffinity purified RSV F protein (50 ng/mL) and 2-fold serial dilutions of immune sera. A goat anti-mouse IgG antibody conjugated to alkaline phosphatase (Jackson ImmunoRes., Mississauga, Ont., Canada) was used as secondary antibody. For the measurement of IgG1 and IgG2a antibody titres, the secondary antibodies used were monospecific sheep anti-mouse IgG1 (Serotec, Toronto, Ont., Canada) and rat anti-mouse IgG2a (Zymed, San Francisco, Calif., USA) antibodies conjugated to alkaline phosphatase, respectively. Plaque reduction titres were determined according to Prince et al (ref. 19) using vaccine quality Vero cells. Four-fold serial dilutions of immune sera were incubated with 50 pfu of RSV, Long strain (ATCC) in culture medium at 37° C. for 1 hr in the presence of 5% $CO_2$. Vero cells were then infected with the mixture. Plaques were fixed with 80% methanol and developed 5 days later using a mouse anti-RSV-F monoclonal IgG1 antibody and donkey antimouse IgG antibody conjugated to peroxidase (Jackson ImmunoRes., Mississauga, Ont. Canada). The RSV-specific plaque reduction titre was defined as the dilution of serum sample yielding 60% reduction in the number of plaques. Both ELISA and plaque reduction assays were performed in duplicates and data are expressed as the means of two determinations. These data were subjected to statistic analysis using SigmaStat (Jandel Scientific Software, Guelph, Ont. Canada).

To examine the induction of RSV-specific CTL following DNA immunization, spleens from 2 immunized mice were removed to prepare single cell suspensions which were pooled. Splenocytes were incubated at $2.5 \times 10^6$ cells/mL in complete RPMI medium containing 10 U/mL murine interleukin 2 (IL-2) with γ-irradiated (3,000 rads) syngeneic splenocytes ($2.5 \times 10^6$ cells/mL) infected with 1 $TCID_{50}$/cell RSV (Long strain) for 2 hr. The source of murine IL-2 was supernatant of a mouse cell line constitutively secreting a high level of IL-2 obtained from Dr. H. Karasuyama of Basel Institute for Immunology (ref. 20). CTL activity was tested 5 days following the in vitro re-stimulation in a standard 4 hr chromium release assay. Target cells were 5 $^{51}$Cr-labelled uninfected BALB/c fibroblasts (BC cells) and persistently RSV-infected HCH14 fibroblasts, respectively. Washed responder cells were incubated with $2 \times 10^3$ target cells at varying effector to target ratios in 200 µL in 96-well V-bottomed tissue-culture plates for 4 hr at 37° C. Spontaneous and total chromium releases were determined by incubating target cells with either medium or 2.5% Triton-X 100 in the absence of responder lymphocytes. Percentage specific chromium release was calculated as (counts–spontaneous counts)/(total counts–spontaneous counts)× 100. Tests were performed in triplicates and data are expressed as the means of three determinations. For antibody blocking studies in CTL assays, the effector cells were incubated for 1 hr with 10 µg/ml final of purified mAb to CD4 (GK1.5) (ref. 21) or mAb against murine CD8 (53-6.7) (ref. 22) before adding chromium labelled BC or BCH4 cells. To determine the effect of anti-class I MHC antibodies on CTL killing, the chromium labelled target cells BC or BCH4 were incubated with 20 µL of culture supernate of hybridoma that secretes a mAb that recognizes $K^d$ and $D^d$ of class I MHC (34-1-2S) (ref. 23) prior to the addition of effector cells.

Example 3

This Example describes the immunogenicity and protection by polynucleotide immunization by the intramuscular route.

To characterize the antibody responses following i.m. DNA administration, immune sera were analyzed for anti-RSV F IgG antibody titre by ELISA and for RSV-specific plaque reduction titre, respectively. All four plasmid constructs were found to be immunogenic. Sera obtained from mice immunized with pXL1–4 demonstrated significant anti-RSV F IgG titres and RSV-specific plaque reduction titres as compared to the placebo group (Table 1 below) (P<0.0061 and <0.0001, respectively, Mann-Whitney Test). However, there is no significant difference in either anti-RSV F IgG titre or RSV-specific plaque reduction titre among mice immunized with either pXL1, pXL2, pXL3 or pXL4.

To evaluate the protective ability of pXL1–4 against primary RSV infection of the lower respiratory tract, immunized mice were challenged intranasally with mouse-adapted RSV and viral lung titres post challenge were assessed. All four plasmid constructs were found to protect animals against RSV infection. A significant reduction in the viral lung titre was observed in mice immunized with pXL1–4 as compared to the placebo group (P<0.0001, Mann-Whitney Test). However, varying degrees of protection were observed depending on the plasmid. In particular, PXL1 was more protective than pXL3 (P=0.00109, Mann-Whitney Test), and pXL4 more than pXL3 (P=0.00125), whereas only pXL2 induced complete protection. This conclusion was confirmed by another analysis with number of fully protected mice as end point (Fisher Exact Test). Constructs pXL1, pXL2 or pXL4 conferred a higher degree of protection than pXL3 (P<0.004, Fisher Exact Test) which was not more effective than placebo. Only pXL2 conferred full protection in all immunized mice.

The above statistical analysis revealed that PXL1 conferred more significant protection than pXL3. The former expresses the truncated and secretory form and the latter the intact membrane anchored form of the RSV F protein. Furthermore, pXL4 was shown to be more protective than pXL3. The difference between these two constructs is the presence of the intron II sequence in pXL4. Construct pXL2 which expresses the secretory form of the RSV-F in the context of the intron II sequence was the only plasmid that confers complete protection in all immunized mice.

Example 4

This Example describes the influence of the route of administration of pXL2 on its immunogenicity and protective ability.

The i.m. and i.d. routes of DNA administration were compared for immunogenicity in terms of anti-RSV F antibody titres and RSV-specific plaque reduction titres. Analyses of the immune sera (Table 2 below) revealed that the i.d. route of DNA administration was as immunogenic as the i.m. route as judged by anti-RSV F IgG and IgG1 antibody responses as well as RSV-specific plaque reduction titres. However, only the i.m. route induced significant anti-RSV F IgG2a antibody responses, whereas the IgG2a isotype titre was negligible when the i.d. route was used. The i.m. and i.d. routes were also compared with respect to the induction of RSV-specific CTL. Significant RSV-specific CTL activity was detected in mice immunized intramuscularly. In contrast, the cellular response was significantly lower in mice inoculated intradermally (Table 3 below). In spite of these differences, protection against primary RSV infection of the lower respiratory tract was observed in both groups of mice immunized via either route (Table 4 below). The CTL induced by RSV-F DNA are classical CD8+class I restricted CTL. The target cells, BCH4 fibroblasts express class I MHC only and do not express class II MHC. Further, prior incubation of BCH4 target cells with anti class-I MHC antibodies significantly blocked the lytic activity of RSV-F DNA induced CTL line. While anti-CD8 antibody could partially block lysis of BCH4 cells, antibody to CD4 molecule had no effect at all (Table 5 below). Lack of total blocking by mAb to CD8 could either be due to CTL being CD8 independent (meaning that even though they are CD8+ CTL, their TCR has enough affinity for class I MHC+peptide and it does not require CD8 interaction with the alpha 3 of class I MHC) or the amount of antibody used in these experiments was limiting. There was no detectable lysis of YAC-1 (NK sensitive target) cells (data not shown).

Example 5

This Example describes immunization studies in cotton rats using pXL2.

The immune response of cotton rats to DNA immunization was analyzed by the protocol shown in Table 6 below. On day −5, 40 cotton rats were randomly selected and divided into 8 groups of 5. Cotton rats in groups 1 and 7 were inoculated intramuscularly (i.m.) into the tiberlia anteria (TA) muscles bilaterally with cardiotoxin (1.0 $\mu$M). On day −1, the cotton rats in group 8 were inoculated in the TA muscles with bupivacaine (0.25%). On day 0, several animals in each group were bled to determine levels of RSV-specific antibodies in the serum of the test animals prior to administration of vaccines. All of the animals were then inoculated i.m. or intradermally (i.d.) with 200 $\mu$g of plasmid DNA, placebo (non-RSV-specific DNA), 100 median cotton rat infectious doses (CPID50; positive control) of RSV, or of formalin inactivated RSV prepared in Hep-2 tissue culture cells and adjuvanted in alum. Forty-four days later the cotton rats in groups 1 & 7 were reinoculated with cardiotoxin in the TA muscles. Four days later (48 days after priming with vaccine), the animals in group 8 were reinoculated with bupivacains in the TA muscle of the right leg. The next day, (seven weeks after priming with vaccine) all of the animals were bled and all, except those in the group given live RSV, were boosted with the same material and doses used on day 0. 29 days later, each cotton rat was bled and then challenged intranasally (i.n.) with 100 CRID50 RSV A2 grown in Hep-2 tissue culture cells. Four days after this virus challenge (day +88) all of the cotton rats were killed and their lungs removed. One lobe from each set of lungs was fixed in formalin and then processed for histologic evaluation of pulmonary histopathology. The remaining lobes of lung will be assessed for the presence and levels of RSV. Each of the sera collected on days 0, 49 and 78 were tested for RSV-neutralizing activity, anti-RSV fusion activity and RSV-specific ELISA antibody.

The RSV neutralizing titres on day +49 and +78 are shown in Tables 7($a$) below and 7($b$) below respectively. As can be seen from the results shown in Table 7($a$), on day +49 the animals immunized with live RSV and DNA immunization had substantial PSV serum neutralizing titres. The animals immunized with formalin-inactivated RSV had a neutralizing titre equivalent to the placebo group on day +49 but following boosting titres by day +78 had reached 5.8 ($\log_{10}/0.05$). Boosting had no significant effect upon animals immunized with live RSV or by i.m. plasmid immunization.

RSV titres in nasal washes (upper respiratory tract) on day +82 are shown in Table 8 below. RSV titres in the lungs (lower respiratory tract) on day +82 are shown in Table 9 below. All of the vaccines provided protection against lung infection but under these conditions, only live virus provided total protection against upper respiratory tract infection.

The lungs from the cotton rats were examined histologically for pulmonary histopathology and the results are shown in Table 10 below. With the exception of lung sections obtained from Group 9 which were essentially free of inflammatory cells or evidence of inflammation, and those from Group 3, which exhibited the maximal pulmonary pathology seen in this study, all of the sections of lung obtained from the other groups looked familiar, i.e. scattered inflammatory cells were present in most fields, and there was some thickening of septae. These are evidence of mild inflammatory diseases. Large numbers of inflammatory cells and other evidence of inflammation were present in sections of lung from Group 3 (in which formalin-inactivated [FI] RSV vaccine was given prior to virus challenge). This result indicated that immunization with plasmid DNA expressing the RSV F protein does not result in pulmonary histopathology different from the placebo, whereas FI-RSV caused more severe pathology.

Example 6

This Example describes the determination of local lung cytokine expression profile in mice imunized with pXL2 after RSV challenge.

Balb/C mice were immunized at 0 and 6 weeks with 100 μg of pXL2, prepared as described in Example 1, and challenged with RSV i.n. at 10 weeks. Control animals were immunized with FI-RSV and live RSV and challenged with RSV according to the same protocol. Four days post viral challenge, lungs were removed from immunized mice and immediately frozen in liquid nitrogen. Total RNA was prepared from lungs homogenized in TRIzol/β-mercaptoethanol by chloroform extraction and isopropanol precipitation. Reverse transcriptase-polymerase chain reaction (RT-PCR) was then carried out on the RNA samples using either IL-4, IL-5 or IFN-γ specific primers from Clone Tech. The amplified products were then liquid-hybridized to cytokine-specific $^{32}$P-labeled probes from Clone Tech, resolved on 5% polyacrylamide gels and quantitated by scanning of the radioactive signals in the gels. Three mouse lungs were removed from each treatment group and analyzed for lung cytokine expression for a minimum of two times. The data is presented in FIG. 9 and represents the means and standard deviations of these determinations.

Figure 9:
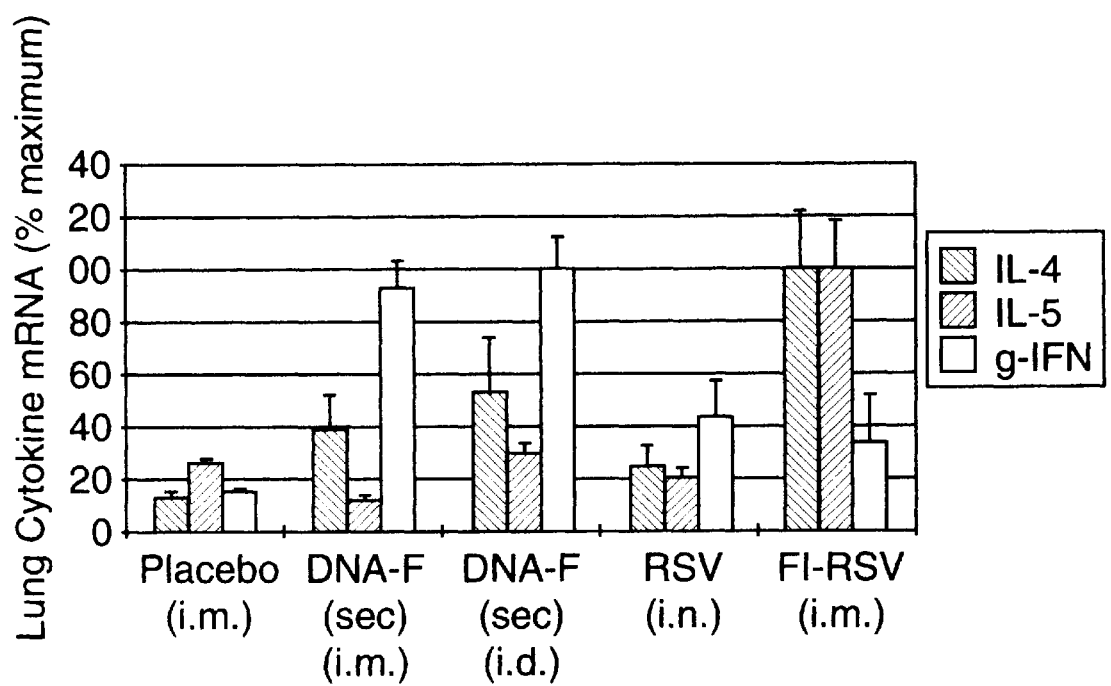
FIG. 9 shows the lung cytokine expression profile in DNA-immunized mice after RSV challenge.

As may be seen from the data presented in FIG. 9:

1. Immunization with live RSV intranasally (i.n.) resulted in a balanced cytokine profile (IFN-γ, IL-4 and IL-5), whereas that with FI-RSV intramuscularly (i.m.) resulted in a Th2 predominance (elevated IL-4 and IL-5). These results are similar to what were reported in the literature.
2. Immunization with pXL2 containing the secretary (sec.) form of FI via either the i.m. or intradermal (i.d.) route gave rise to a balanced cytokine profile similar to that with live RSV immunization.
3. The magnitude of the cytokine responses with i.m. and i.d. immunication using pXL2 expressing a secretory form of the protein in significantly higher than that with live RSV immunization.

Example 7

This Example describes the construction of a plasmid vector encoding the RSV F protein and containing the 5' UTR and signal peptide of Herpes Simplex Virus I (HSV I)gD.

Figure 10:
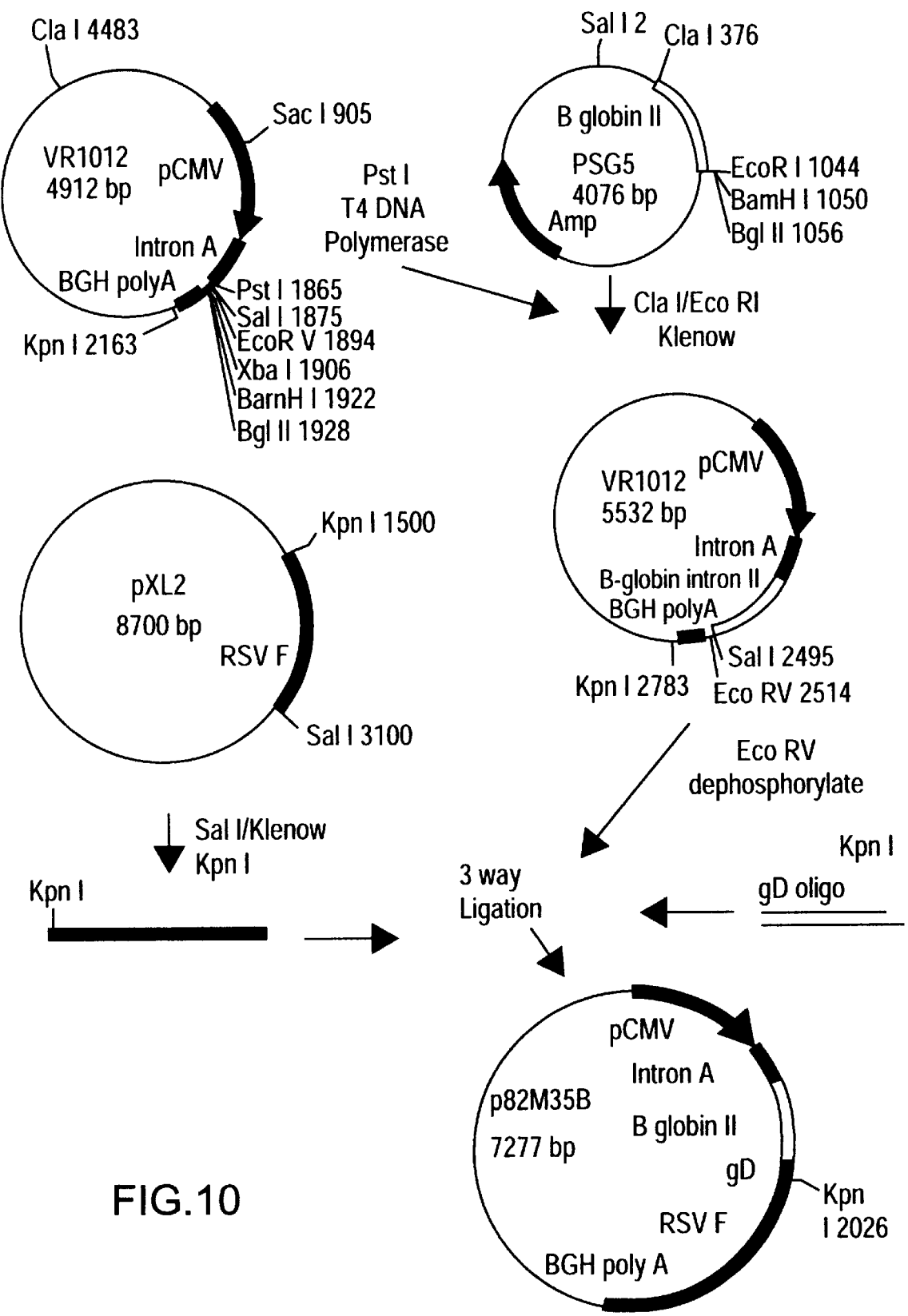
FIG. 10 is a schematic showing the assembly of plasmid p82M35B containing a gene encoding a secreted form of the RSV F protein lacking the transmembrane region, the rabbit β-globin Intron II sequence and the signal peptide sequence HSV I gD.

Plasmid p82M35B was prepared following the scheme shown in FIG. 10. Plasmid pVR1012 (Vical) (FIG. 11; SEQ ID No: 6) containing the CMV promoter, intron A, and the BGH poly A sequences, was linearized with restriction enzyme Pst I and made blunt ended with T4 DNA polymerase. The rabbit β-globin intron II sequence was retrieved from plasmid pSG5 (Stratagene; ref. 14) by Cla I and Eco RI digestion, and the 0.6 kb fragment was isolated and made blunt ended by treatment with Klenow fragment polymerase. The rabbit β-globin intron II fragment was then ligated to the Pst I/blunt ended VR1012 plasmid (FIG. 10). This vector was then restricted with Eco RV and dephosphorylated.

The secreted form of RSV F was isolated from plasmid pXL2 (Example 1; FIG. 5) by digestion with Sal I, made blunt end by treatment with Klenow fragment polymerase, then restricted with Kpn I to produce a 5' Kpn I, 3'blunt ended fragment. The HSV gD sequence was synthesized as a synthetic oligonucleotide having the DNA (SEQ ID No: 7) and derived amino acid (SEQ ID No: 8) sequence shown in FIG. 12.

The gD oligonucleotide has a 5' blunt end and 3' Kpn I recognition sequence. A three-way ligation was performed with the isolated RSV F fragment, gD oligo and the VR1012 plasmid, to produce plasmid p82M35B (FIG. 10).

Example 8

This Example illustrates the expression and secretion of RSV F protein in vitro.

BHK cells were transfected with either p82M35B, its counterpart containing the autologous RSV F signal peptide (pXL2) or the vector backbone alone (placebo) using Lipofectin (Gtibco/BRL). Forty-eight hours post transfection, supernatant fractions were recovered and subjected to RSV F protein quantification using a F-specific enzyme-linked immunoabsorbent assay (ELISA). Three independent transfection assays were performed for each vector.

ELISAs were performed using one affinity-purified mouse monoclonal anti-RSV F antibody (2 μg/ml) as the capturing reagent and another biotinolated monoclonal anti-RSV F antibody (0.1 μg/ml) as the detection reagent. Horseradish peroxidase-labelled avidin (Pierce) was subsequently used. The RSV F standard protein used was purified from detergent-lysates of cultured virus by immunoaffinity chromatography.

Table 11 (below) shows the results obtained. As seen in Table II, compared to placebo, both p82M35B and pXL2 mediated significant F protein expression/secretion from the BHK cells 48 hours post transfection. Furthermore, a markedly higher level of the F protein was consistently detected in the supernatant fraction of p82M35B-transfected BHK cells than that of pXL2-transfected cells, representing a 5.4-fold improvement over the latter. These results indicate that replacement of the coding sequence for the autologous RSV F signal peptide with that for the 5'UTR and signal peptide of HSV I gD significantly enhanced F protein expression/secretion in vitro.

Example 9

This Example illustrates immunogenicity studies carried out using p82M35B.

Tibialis anterior muscles of BALB/c mice (male, 6 to 8 weeks old) (Jackson Lab., Bar Harbor, Me., USA) were bilaterally injected with 2×50 μg (1 μg/μL in PBS) of p82M35B, pXL2 or the vector backbone alone (placebo). In some groups, 5 days prior to DNA injection, the muscles were treated with 2×50 μL (10 μM in PBS) of cardiotoxin (Latoxan, France) to increase DNA uptake and enhance immune responses as reported by Davis et al., (ref. 24). The animals were boosted with the same dose of plasmid DNA 6 weeks later. Mice in the positive control group were immunized intranasally (i.n.) with $10^6$ plaque forming units (pfu) of a clinical RSV strain of the A2 subtype grown in Hep2 cells kindly provided by Dr. B. Graham (ref. 16).

Antisera obtained from immunized mice were analyzed for anti-RSV F IgG antibody titres using specific ELISA and for RSV-specific plaque-reduction titres. ELISAs were performed using 96-well plates coated with immunoaffinity-purified RSV F protein (50 ng/mL) and 2-fold serial dilutions of immune sera. A goat anti-mouse IgG antibody conjugated to alkaline phosphatase (Jackson ImmunoRes., Mississauga, Ont., Canada) was used as secondary antibody. Plaque reduction titres were determined according to Prince et al. (ref. 19) using vaccine-quality Vero cells. Four-fold serial dilutions of immune sera were incubated with 50 pfu of the RSV Long strain (ATCC) in culture medium at 37° C. for 1 hr in the presence of 5% $CO_2$ and the mixtures were used to infect Vero cells. Plaques were fixed with 80% methanol and developed 5 days later using a mouse anti-RSV F monoclonal IgG1 antibody and donkey anti-mouse IgG antibody conjugated to peroxidase (Jackson ImmunoRes. Mississauga, Ont.). The RSV-specific plaque reduction titre was defined as the dilution of serum sample yielding 60% reduction in plaque number. Both ELISAs and plaque reduction assays were performed in duplicate and data are expressed as the means of two determinations.

The results of these studies are set forth in Table 12 below. For the induction of serum antibody responses (Table 12), p82M35B is effective without the need of cardiotoxin pretreatment under the DNA dose and immunization regimen used, resulting in anti-F IgG titre of 7.2±1.1 ($log_2$ titre/100) and RSV-specific plaque reduction titre of 11.8±0.9 ($log_2$) after two immunizations. In contrast, the antibody titres elicited by pXL2 in the absence of the cardiotoxin pretreatment were significantly lower (IgG titre of 2.9±2.3 and plaque reduction titre of 8.2±1.9). However, serum antibody responses elicited by pXL2 were significantly improved with the cardiotoxin pretreatment step (IgG titre of 7.4±1.1 and plaque reduction titre of 10.5±0.8). The placebo was unable to elicit a detectable serum antibody response in the absence or presence of the cardiotoxin pretreatment step.

This trend was extendible to results of the protection study (Table 12). Vector p82M35B conferred full protection against RSV infection of lungs in the absence of the cardiotoxin pretreatment. In contrast, pXL2 only conferred partial protection under the same conditions. However, full protection was achieved with the pXL2 vector when cardiotoxin pretreatment step was included in the immunization regimen. No protection was observed with the placebo with or without the cardiotoxin pretreatment step.

These results show the replacement of the coding sequence for the autologous RSV F signal peptide with that for the 5'UTR and signal peptide of HSV I gD resulted in significant enhancement in not only F protein expression/secretion assessed in vitro (Example 8), but also immunogenicity to the F protein as well as protective ability against RSV infection assessed in the mouse model.

SUMMARY OF THE DISCLOSURE

In summary of this disclosure, the present invention provides certain novel vectors containing genes encoding an RSV F proteins, methods of immunization using such vectors and methods of diagnosis using such vectors. Modifications are possible within the scope of this invention.

TABLE 1

Immunogenic and Protective Abilities of pXL1-4 Mice via the i.m. Route

| Plasmid DNA Immunogen | No. Mice | Mean Anti-RSV F ELISA Titre (IgG)* ($Log_2/100 \pm SD$) | Mean Plaque Reduction Titre* ($Log_4 \pm SD$) | Post RSV Challenge | |
|---|---|---|---|---|---|
| | | | | Mean Virus Lung Titre# (pfu/g lung) ($Log_{10} \pm SD$) | No. Fully Protected Mice** |
| pXL1 | 8 | 3.00 ± 1.85 | 3.74 ± 0.98 | 0.72 ± 0.99 | 5 |
| pXL2 | 9 | 5.78 ± 1.72 | 4.82 ± 0.51 | 0.00 ± 0.00 | 9 |
| pXL3 | 8 | 3.75 ± 2.05 | 4.59 ± 1.16 | 2.77 ± 0.72 | 0 |
| pXL4 | 9 | 5.44 ± 1.13 | 5.18 ± 0.43 | 0.66 ± 1.00 | 6 |
| Placebo** | 12 | 0.58 ± 2.89 | 0.18 ± 0.62 | 3.92 ± 0.27 | 0 |

*These sets of data from sera obtained 1 week prior to the viral challenge
Detection sensitivity of the assay was $10^{1.96}$ pfu/g lung.
**The term, fully protected mice, refers to animals with no detectable RSV in lungs post challenge.

TABLE 2

Immunogenicity of pXL2 in Mice*

| Route | No. Mice | Mean Anti-RSV F ELISA Titre ($Log_2/100 + SD$) | | | Mean Plaque Reduction Titre ($Log_4 \pm SD$) |
|---|---|---|---|---|---|
| | | IgG | IgG1 | IgG2a | |
| i.m | 8 | 7.63 ± 0.92 | 4.25 ± 1.91 | 4.38 ± 1.92 | 4.18 ± 0.88 |
| i.d. | 7 | 7.00 ± 1.00 | 5.00 ± 1.00 | 0.14 ± 0.38 | 3.65 ± 0.59 |
| Placebo(i.m.) | 9 | 0.50 ± 0.51 | 0.00 ± 0.00 | 0.00 ± 0.00 | 0.18 ± 0.50 |

*These sets of data are from sera obtained 1 week prior to the viral challenge.

TABLE 3

Induction of RSV-specific CTL Following DNA Immunization*

| Route | E:T Ratio | % Specific Lysis BC | % Specific Lysis BCH4 |
|---|---|---|---|
| i.m. | 200:1 | 23.3 | 100.6 |
|  | 100:1 | 17.0 | 62.4 |
|  | 50:1 | 19.9 | 64.1 |
|  | 25:1 | 22.3 | 46.4 |
| i.d. | 100:1 | 20.9 | 26.1 |
|  | 50:1 | 21.7 | 19.1 |
|  | 25:1 | 7.1 | 7.0 |
|  | 12.5:1 | 2.8 | 2.3 |

*These set of data were obtained from immunized mice immediately prior to RSV challenge.

TABLE 4

Immunoprotective Ability of pXL2 in Mice

| Route | No. Mice | Post RSV Challenge Mean Virus Lung Titre* (pfu/g lung) | No. Fully Protected Mice# |
|---|---|---|---|
| i.m. | 8 | 0.00 ± 0.00 | 8 |
| i.d. | 7 | 0.43 ± 1.13 | 6 |
| Placebo (i.m.) | 9 | 4.30 ± 022 | 0 |

*Detection sensitivity of the assay was 101.69 pfu/g lung.

The term, fully protected mice, refers to animals with no detectable RSV in lungs post challenge.

TABLE 5

RSV specific CTL included by i.m. DNA immunization are class I restricted CTL

| E:T Ratio | BCH4 | BCH4 + anti-CD4 | BCH4 + anti-CD8 | BCH4 + anti-class I MHC |
|---|---|---|---|---|
| 100:1 | 52.03 | 54.3 | 39.4 | 8.6 |
| 50:1 | 44.4 | 47.2 | 27.4 | 6.2 |
| 25:1 | 28.6 | 26.3 | 14.8 | 1 |
| 12.5:1 | 18.2 | 15 | 8 | −2.7 |

TABLE 6

| Group | Antigen | RSV-specific dose | Inoc. route | Pretreatment/ Adjuvant | Day 0 | Day 49 | Day 78 | Day 88 |
|---|---|---|---|---|---|---|---|---|
| 1 | Placebo | 0 | I.M. | Cardiotoxin | Prebleed, several cotton rats per group; prime all animals | Bleed all animals; boost all except those in group 2 | Challenge with RSV A2 I.N. after bleeding all | Harv. animals and do histologic evaluation, pulmonary virus titers, antibodies |
| 2 | Live RSV | 100 CRID50 | I.N. | None | | | | |
| 3 | FI-RSV | | I.M. | Alum | | | | |
| 5 | pXL2 | 200 μg | I.M. | None | | | | |
| 6 | pXL2 | 200 μg | I.D. | None | | | | |
| 7 | pXL2 | 200 μg | I.M. | Cardiotoxin | | | | |
| 8 | pXL2 | 200 μg | I.M. | Bupivacaine | | | | |

TABLE 7(a)

RSV Serum Neutralizing Titers on Day 49

| Group | Antigen | RSV-specific dose | Inoc. route | Nt. antibody titer (log₂/0.05 ml) in CR no. 1 | 2 | 3 | 4 | Mean titer log2/ 0.05 | Stand. Dev. |
|---|---|---|---|---|---|---|---|---|---|
| 1 | Placebo | 0 | I.M. | 4 | 3 | 2 | 2 | 2.75 | 1.0 |
| 2 | Live RSV | 100 CRID50 | I.N. | 9 | 9 | 9 | 9 | 9 | 0.0 |

TABLE 7(a)-continued

RSV Serum Neutralizing Titers on Day 49

| Group | RSV-specific Antigen | Inoc. dose | route | Nt. antibody titer (log$_2$/0.05 ml) in CR no. 1 | 2 | 3 | 4 | Mean titer log2/ 0.05 | Stand. Dev. |
|---|---|---|---|---|---|---|---|---|---|
| 3 | FI-RSV | | I.M. | 0 | 4 | 2 | 2 | 2.0 | 1.6 |
| 5 | pXL2 | 200 μg | I.M. | 9 | 8 | 8 | 7 | 8.0 | 0.8 |
| 6 | pXL2 | 200 μg | I.D. | 5 | 2 | 5 | 5 | 4.3 | 1.5 |
| 7 | pXL2 | 200 μg | I.M. | 8 | 8 | 9 | 9 | 8.5 | 0.6 |
| 8 | pXL2 | 200 μg | I.M. | 8 | 9 | 6 | 6 | 7.3 | 1.5 |

TABLE 7(b)

RSV Serum Neutralizing Titers on Day 78

| Group | RSV-specific Antigen | Inoc. dose | route | Nt. antibody titer (log$_2$/0.05 ml) in CR no. 1 | 2 | 3 | 4 | Mean titer log$_2$/ 0.05 | Stand. Dev. |
|---|---|---|---|---|---|---|---|---|---|
| 1 | Placebo | 0 | I.M. | 3 | 2 | 4 | Died | 3.0 | 1.0 |
| 2 | Live RSV | 100 CRID50 | I.N. | 8 | 9 | 8 | 9 | 8.5 | 0.6 |
| 3 | FI-RSV | | I.M. | 8 | 4 | 6 | 5 | 5.8 | 1.7 |
| 5 | pXL2 | 200 μg | I.M. | 7 | 8 | 8 | 8 | 7.8 | 0.5 |
| 6 | pXL2 | 200 μg | I.D. | 8 | 6 | 6 | Died | 6.7 | 1.2 |
| 7 | pXL2 | 200 μg | I.M. | 8 | 9 | 9 | 8 | 8.7 | 0.6 |
| 8 | pXL2 | 200 μg | I.M. | 8 | 7 | 9 | 9 | 8.3 | 1.0 |

TABLE 8

RSV Titers in Nasal Washes on Day 82

| Group | RSV-specific Antigen | Inoc. dose | route | RSV titer (log$_{10}$/0.05 ml) in cotton rat no. 1 | 2 | 3 | 4 | Mean titer log$_{10}$/ 0.05 | Stand. Dev. |
|---|---|---|---|---|---|---|---|---|---|
| 1 | Placebo | 0 | I.M. | 3.4 | 3.3 | 3.3 | Died | 3.3 | 0.1 |
| 2 | Live RSV | 100 CRID50 | I.N. | 0 | 0 | 0 | 0 | 0.0 | 0.0 |
| 3 | FI-RSV | | I.M. | 0 | 0 | 2.8 | 0 | 0.7 | 1.4 |
| 5 | pXL2 | 200 μg | I.M. | 3.3 | 2.3 | 3.3 | 2.3 | 2.8 | 0.6 |
| 6 | pXL2 | 200 μg | I.D. | N.D. | N.D. | N.D. | Died | N.D. | N.D. |
| 7 | pXL2 | 200 μg | I.M. | 2.3 | 0 | 0 | 3.2 | 1.4 | 1.6 |
| 8 | pXL2 | 200 μg | I.M. | N.D. | N.D. | N.D. | N.D. | N.D. | N.D. |

N.D. = non-determined

TABLE 9

Titers in Lungs on Day 82

| Group | RSV-specific Antigen | Inoc. dose | route | RSV titer (log$_{10}$/g lung) in cotton rat no. 1 | 2 | 3 | 4 | Mean titer log$_{10}$/ | Stand. Dev. |
|---|---|---|---|---|---|---|---|---|---|
| 1 | Placebo | 0 | I.M. | 4.7 | 4.2 | 3.7 | Died | 4.2 | 0.5 |
| 2 | Live RSV | 100 CRID50 | I.N. | 0 | 0 | 0 | 0 | 0.0 | 0.0 |
| 3 | FI-RSV | 10$^5$ PFU | I.M. | 0 | 0 | 0 | 0 | 0.0 | 0.0 |
| 5 | pXL2 | 200 μg | I.M. | 0 | 2.2 | 0 | 0 | 0.6 | 1.1 |
| 6 | pXL2 | 200 μg | I.D. | 0 | 2.2 | 2.7 | 3.2 | 2.0 | N.D. |
| 7 | pXL2 | 200 μg | I.M. | 0 | 0 | 0 | 0 | 0.0 | 0.0 |
| 8 | pXL2 | 200 μg | I.M. | 0 | 0 | 0 | 0 | 0.0 | N.D. |

N.D. = non-determined

TABLE 10

Summary of Histopathology Results Seen in Sections of Cotton Rat Lung

| Group | Treatment | Major Observations & Comments |
|---|---|---|
| 1. | Placebo + RSV | Scattered individual and groups of macrophages and polymorphonuclear neutrophiles (PMN) in all fields. Overt thickening of septae. Occasional pyknotic cells seen. Overall: mild to moderate inflammation. |
| 2. | Live RSV | Isolated macrophages seen in most fields. Scattered PMN. Overall: minimal inflammation |
| 3. | HRSV + RSV | Virtually every field contains numerous mononuclear cells & PMN. Pyknotic cells and debris common. Thickened septae. Evidence of exacerbated disease. |
| 5. | Plasmid + RSV | Isolated macrophages seen in most fields. Occasional PMN seen. Very similar to live virus group. |
| 6. | Plasmid i.d. + RSV | Isolated macrophages seen in most fields. Occasional PMN seen. |
| 7. | Plasmid + CT + RSV | Isolated mononuclear cells and PMN seen in most fields. |
| 8. | Plasmid + Biv + RSV | Scattered mononuclear cells and PMN seen in most fields. |
| 9. | Normal CR Lung | Few leukocytes evidence. Airy, open appearance. Thin septae. |

CT = carditoxin
Biv = bupivacaine

TABLE 11

Expression/Secretion of the RSV F protein from BHK cells (48 hr post transfection)

| Plasmid Construct | F Protein Secretion (mean ± S.D.) (ng/mL) | Magnitude of Improvement |
|---|---|---|
| Placebo | 0.0 ± 0.0 | |
| p82M35B | 32.1 ± 2.06 | 5.4 x (over pXL2) |
| pXL2 | 5.9 ± 0.6 | |

TABLE 12

Immunoprotective Ability of DNA-F in BALB/c Mice

| Immunogen | Anti-F IgG Titre Log2 (titre/100) 10 weeks | RSV-Specific Plaque Reduction Titre (Log2 titre) | Mean Virus Lung Titre* (pfu/g lung) (Log2 10 ± SD) | No. Fully protected # No. Immunized |
|---|---|---|---|---|
| Placebo (i.m.) | 0.0 ± 0.0 | 0.0 ± 0.0 | 4.3 ± 0.5 | 0/6 |
| p82M35B (i.m.) | 7.2 ± 1.1 | 11.8 ± 0.9 | 0.0 ± 0.0 | 6/6 |
| pXL2 (i.m.) | 2.9 ± 2.3 | 8.2 ± 1.9 | 2.9 ± 1.7 | 1/6 |
| pXL2 + cardiotoxin | 7.4 ± 1.1 | 10.5 ± 0.8 | 0.0 ± 0.0 | 6/6 |
| RSV (i.n.) | 8.5 ± 2.7 | 12.4 ± 0.7 | 0.0 ± 0.0 | 6/6 |

*Sensitivity of assay: 101.69 pfu/g lung.
The term, fully protected mice, refers to animals with no detectable RSV in the lungs 4 days post viral challenge.

REFERENCES

1. McIntosh K., Canock, R. M. In: Fields B N, Knipe, D M, editors. Virology. New York: Raven Press: 1990: 1045–1072.
2. Katz S L., In: New Vaccine Development establishing priorities. Vol. 1. Washington: National Academic Press: 1985: 397–409.
3. Wertz G W, Sullender W M., Biotechnology 1992; 20: 151–176.
4. Johnson et al., J. Virol 1987, 61: 3163–3166.
5. Pemberton et al., J. Gen Virol. 1987, 68: 2177–2182.
6. Crowe, J. E., Vaccine 1995, 13: 415–421.
7. WO 90/11092
8. WO 94/21797
9. Ulmer, Current Opinion, Invest Drugs, 1993, 2: 983–989.
10. Tang et al., Nature 1992, 356: 152–154.
11. Furth et al. Analytical Biochemistry, 1992, 205: 365–368.
12. Pizzorno et al., J. Virol. 1988, 62: 1167–1179.
13. Chapman, B. S.; Thayer, R. M.; Vincent, K. A. and Haigwood, N. L., Nucl. Acids. Res. 1991, 19: 3979–3986.
14. Green, S. Isseman, I., and Sheer, E., Nucl. Acids. Res. 1988, 16: 369.
15. Breathnack, R. and Harris, B. A., Nucl. Acids Res. 1983, 11: 7119–7136.
16. Graham, B. S.; Perkins M. D.; Wright, P. F. and Karzon, D.T. J. Mod. Virol. 1988 26: 153–162.
17. Nabel, G. J. 1993, Proc. Natl. Acad. Sci. USA 90: 11307–11311.
18. Du, R. P et al. 1994., Biotechnology 12: 813–818.
19. Prince, G. A. et al, 1978. Ame. J. Pathol. 93: 771–790.
20. Karasuyama & Melchers, Eur. J. Immunol. 18, 97–104, 1988.
21. Wilde, David et al. 1983. J. Immunol. 131: 2178–2183.

22. Ledbetter, J. A., Rouse R., Micklem, H. 1980, J. Exp. Med. 152: 280–295

23. Ozato Kerko et al. 1982, Transplantation 34: 113–118.

24. Davis et al., Vaccine 1994, 12: 1503–1509

---

What we claim is:

1. A method of immunizing a host against disease caused by infection with respiratory syncytial virus (RSV), which comprises administering to said host an effective amount of a plasmid vector comprising a nucleotide sequence encoding an RSV F protein fragment that generates antibodies and/or cytotoxic T-lymphocytes (CTLs) that specifically react with RSV F protein, said RSV F protein fragment lacking an autologous RSV F signal peptide sequence and including a sequence encoding a heterologous signal peptide which enhances the level of expression of RSV F protein, and a promoter sequence operatively coupled to said nucleotide sequence for expression of said RSV F protein fragment in said host.

2. The method of claim 1 wherein said nucleotide sequence encodes a RSV F protein fragment lacking a transmembrane region.

3. The method of claim 1 wherein the nucleotide sequence encoding a signal peptide encodes a Herpes Simplex Virus I gD signal peptide.

4. The method of claim 1 wherein said host is a human.

5. The method of claim 1 wherein said plasmid vector further comprises a further nucleotide sequence located adjacent said nucleotide sequence to enhance the immunoprotective ability of said RSV F protein fragment when expressed in vivo from said vector in said host, wherein said further nucleotide sequence comprises a pair of splice sites to prevent aberrant mRNA splicing.

6. The method of claim 4 wherein said promoter sequence is an immediate early cytomegalovirus promoter.

7. The method of claim 5 wherein said promoter sequence is an immediate early cytomegalovirus promoter.

8. The method of claim 5 wherein said vector is p82M35B as shown in FIG. 10.

9. The method of claim 7 wherein said further nucleotide sequence is located between said nucleotide sequence and said promoter sequence.

10. The method of claim 8 wherein said further nucleotide sequence is that of rabbit β-globulin intron II.

11. A method of using a gene encoding an RSV F protein fragment that generates antibodies and/or cytotoxic T-lymphocytes (CTLs) that specifically react with RSV F protein and which lacks an autologous RSV F signal peptide and includes a sequence encoding a heterologous signal peptide which enhances the level of expression of RSV F protein to produce an immune response in a host, which comprises:

isolating said gene;

operatively linking said gene to at least one promoter sequence to produce a plasmid vector, said promoter sequence directing expression of said RSV F protein fragment when said vector is introduced into a host to produce an immune response to said RSV F protein fragment; and introducing said vector into the host.

12. The method of claim 11, wherein said gene encoding an RSV F protein fragment encodes an RSV F protein fragment lacking the transmembrane region.

13. The method of claim 11 wherein said sequence encoding a heterologous signal peptide encodes a Herpes Simplex Virus I gD signal peptide.

14. The method of claim 11 wherein said at least one promoter sequence comprises the immediately early cytomegalovirus promoter.

15. The method of claim 11 wherein said gene is contained within plasmid vector p82M35B (ATCC 203790).

16. The method of claim 12 wherein said at least one promoter sequence comprises the immediate early cytomegalovirus promoter.

17. The method of claim 14 including the step of:

operatively linking said gene to an immunoprotective enhancing sequence comprising a pair of splice sites to prevent aberrant mRNA splicing to produce an enhanced immunoprotection to said RSV F protein in said host.

18. The method of claim 17 wherein said immunoprotective enhancing sequence is introduced into said vector between said control sequence and said gene.

19. The method of claim 17 wherein said immunoprotective enhancing sequence is that of rabbit β-globin intron II.

20. A method of producing a vaccine for protection of a host against disease caused by infection with respiratory syncytial virus (RSV), which comprises:

isolating a first nucleotide sequence encoding an RSV F protein fragment that generates antibodies and/or cytotoxic T-lymphocytes (CTLs) that specifically react with RSV F protein and which lacks an autologous RSV F signal peptide and includes a sequence encoding a heterologous signal peptide which enhances the level of expression of RSV F protein;

operatively linking said first nucleotide sequence to at least one promoter sequence to produce a plasmid vector, the promoter sequence directing expression of said RSV F protein when introduced into a host to produce an immune response to said RSV F protein;

operatively linking said first nucleotide sequence to a second nucleotide sequence to enhance the immunoprotective ability of said RSV F protein when expressed in vivo from the vector in a host, said second nucleotide sequence being introduced into said vector between said promoter sequence and said gene and comprising a pair of splice sites to prevent aberrant mRNA splicing, and formulating said vector as a vaccine for in vivo administration.

21. The method of claim 20 wherein said plasmid vector is p82M35B ATCC 203790).

22. A vaccine produced by the method of claim 20.

23. A method of producing a vaccine for protection of a host against disease caused by infection with respiratory syncytial virus (RSV), which comprises:

isolating a nucleotide sequence encoding an RSV F protein fragment from which the transmembrane region is absent and which lacks an autologous RSV F signal peptide and includes a sequence encoding a heterologous signal peptide which enhances the level of expression of RSV F protein;

operatively linking said nucleotide sequence to at least one promoter sequence to produce a plasmid vector, the promoter sequence directing expression of said RSV F protein when introduced into a host to produce an immune response to said RSV F protein; and formulating said vector as a vaccine for in vivo administration.

24. The method of claim 23 wherein said plasmid vector is p82M35B.

25. A vaccine produced by the method of claim 23.

* * * * *